United States Patent
Schally et al.

(10) Patent No.: US 8,691,942 B2
(45) Date of Patent: Apr. 8, 2014

(54) N- AND C- TERMINAL SUBSTITUTED ANTAGONISTIC ANALOGS OF GH-RH

(75) Inventors: Andrew V. Schally, Miami Beach, FL (US); Marta Zarandi, Miami Beach, FL (US); Jozsef L. Varga, Miami Beach, FL (US); Ren Zhi Cai, Miami, FL (US)

(73) Assignees: University of Miami, Miami, FL (US); U.S.A. Represented by the Dept. of Veterans Affairs, Washington, DC (US)

( * ) Notice: Subject to any disclaimer, the term of this patent is extended or adjusted under 35 U.S.C. 154(b) by 0 days.

(21) Appl. No.: 12/890,626

(22) Filed: Sep. 25, 2010

(65) Prior Publication Data

US 2013/0261055 A1 Oct. 3, 2013

Related U.S. Application Data

(63) Continuation-in-part of application No. PCT/US2009/038351, filed on Mar. 26, 2009.

(60) Provisional application No. 61/305,737, filed on Feb. 18, 2010, provisional application No. 61/040,418, filed on Mar. 28, 2008.

(51) Int. Cl.
*C07K 14/60* (2006.01)
*A61K 38/25* (2006.01)

(52) U.S. Cl.
CPC *C07K 14/60* (2013.01); *A61K 38/25* (2013.01)
USPC .......................................... 530/324; 514/11.2

(58) Field of Classification Search
None
See application file for complete search history.

(56) References Cited

U.S. PATENT DOCUMENTS

| | | | |
|---|---|---|---|
| 4,659,693 A | 4/1987 | Nester | |
| 4,914,189 A | 4/1990 | Schally et al. | |
| 5,084,555 A | 1/1992 | Coy et al. | |
| 5,550,212 A | 8/1996 | Zarandi et al. | |
| 5,942,489 A | 8/1999 | Schally et al. | |
| 7,452,865 B2 | 11/2008 | Schally et al. | |
| 8,227,405 B2 | 7/2012 | Schally et al. | |
| 8,227,421 B2 | 7/2012 | Schally et al. | |
| 2007/0042950 A1 | 2/2007 | Schally et al. | |

FOREIGN PATENT DOCUMENTS

| | | | |
|---|---|---|---|
| WO | WO 91/16923 A1 | 11/1991 | |
| WO | WO 97/42223 A1 | 11/1997 | |
| WO | WO 00/31136 A1 | 6/2000 | |
| WO | PCT/US2005/016953 A2 * | 2/2005 | |
| WO | WO 2009/120831 A2 * | 10/2009 | |
| WO | WO 2011/034976 A1 | 3/2011 | |
| WO | PCT/US2013/048381 | 6/2013 | |

OTHER PUBLICATIONS

Bellyei et al. ("GHRH antagonists reduce the invasive and metastatic potential of human cancer cell lines in vitro," Cancer Letters 293 (2010) 31-40, published online Jan. 12, 2010).*

Auerbach et al., Angiogenesis assays: problems and pitfalls, *Cancer Metastasis Reviews*, (2000), 19:167-172.
Cervini et al., Human growth hormone-releasing hormone hGHRH (1-29)-NH2: systematic structure-activity relationship studies, *Journal of Medicinal Chemistry*, (Feb. 26, 1998), 41(5):717-727.
Dermer, Another Anniversary for the War on Cancer, *Bio/Technology*, (Mar. 12, 1994), 12:320.
Freshney, Cultures of Animal Cells, A Manual of Basic Technique, *Alan R. Liss, Inc.*, (1983), 3-4.
Gura, Systems for identifying new drugs are often faulty, *Science*, New York, New York, (Nov. 1997), 278(5340):1041-1042.
Halmos et al., Human renal cell carcinoma expresses distinct binding sites for growth hormone-releasing hormone, *Proceedings of the National Academy of Sciences of USA*, (Sep. 12, 2000), 97(19):10555-10560.
Jaffe et al., Suppression of Growth Hormone (GH) Hypersecretion due to Ectopic GH-Releasing Hormone (GHRH) by a Selective GHRH Antagonist, *The Journal of Clinical Endorcrinology & Metabolism*, (Feb. 1, 1997), 82(2):634-637.
Jain et al., Quantitative angiogenesis assays: progress and problems, *Nature Medicine*, (Nov. 1997), 3(11):1203-1208.
Kiaris et al., Expression of a splice variant of the receptor for GHRH in 3T3 fibroblasts activates cell proliferation responses to GHRH analogs, *Proceedings of the National Academy of Sciences of USA*, (Jan. 2, 2002), 99(1):196-200.
Klukovits et al., Novel Antagonists of Growth Hormone-Releasing Hormone Inhibit Growth and Vascularization of Human Experimental Ovarian Cancers; *Cancer*, (Feb. 1, 2012), 118(3):670-680.
Letsch et al., Growth hormone-releasing hormone (GHRH) antagonists inhibit the proliferation of androgen-dependent and independent prostate cancers, *Proceedings of the National Academy of Sciences of USA*, (Jan. 23, 2003), 100(3):1250-1255.
Merrifield, Solid Phase Peptide Synthesis. I. The Synthesis of a Tetrapeptide, *Journal of the American Chemical Society*, (1963), 85(14):2149-2154.
MSNBC New Services, Mixed results on new cancer drug, Nov. 9, 2000, 1-4.
Perez et al., Antagonists of growth hormone-releasing hormone suppress in vivo tumor growth and gene expression in triple negative breast cancers, *Oncotarget*, (Sep. 2012), 3(9):988-997.
Plonowski et al., Inhibition of proliferation of PC-3 human prostate cancer by antagonists of growth hormone-releasing hormone: Lack of correlation with the levels of serum IGF-I and expression of tumoral IFG-II and vascular endothelial growth factor, *The Prostate*, (Aug. 2002), 52(3):173-182.
Pozsgai et al., The effect of GHRH antagonists on human glioblastmoas and their mechanism of action; *International Journal of Cancer*, (Nov. 15, 2010), 127(10):2313-2322.

(Continued)

*Primary Examiner* — Christina Bradley
(74) *Attorney, Agent, or Firm* — Pepper Hamilton LLP

(57) ABSTRACT

There is provided a novel series of synthetic analogs of hGH-RH(1-29)NH$_2$ (SEQ ID NO: 1) and hGH-RH(1-30)NH$_2$. Of particular interest are those carrying PhAc, N-Me-Aib, Dca, Ac-Ada, Fer, Ac-Amc, Me-NH-Sub, PhAc-Ada, Ac-Ada-D-Phe, Ac-Ada-Phe, Dca-Ada, Dca-Amc, Nac-Ada, Ada-Ada, or $CH_3$—$(CH_2)_{10}$—CO-Ada, at the N-Terminus and β-Ala, Amc, Apa, Ada, AE$_2$A, AE$_4$P, ε-Lys(α-NH$_2$), Agm, Lys(Oct) or Ahx, at the C-terminus. These analogs inhibit the release of growth hormone from the pituitary in mammals as well as inhibit the proliferation of human cancers, and inhibit the hyperplastic and benign proliferative disorders of various organs, through a direct effect on the cancerous and non-malignant cells. The stronger inhibitory potencies of the new analogs, as compared to previously described ones, result from replacement of various amino acids.

9 Claims, 1 Drawing Sheet

(56) References Cited

OTHER PUBLICATIONS

Pozsgai et al., The effect of novel antagonist of growth hormone releasing hormone on cell proliferation and on the key cell signaling pathways in none different breast cancer cell lines; *International Journal of Oncology*, (Oct 2011), 39(4):1025-32.

Rekasi et al., Antagonists of Growth Hormone-Releasing Hormone and Vasoactive Intestinal Peptide Inhibit Tumor Proliferation by Different Mechanisms: Evidence from in Vitro Studies of Human Prostatic and Pancreatic Cancers, *Endorcrinology*, (Jun. 1, 2000), 141(6):2120-2128.

Rekasi et al., Isolation and sequencing of cDNAs for splice variants of growth hormone-releasing hormone receptors from human cancers, *Proceedings of the National Academy of Sciences of USA*, (Sep. 12, 2000), 97(19):10561-10566.

Schally et al., Antagonistic analogs of growth hormone-releasing hormone: New potential antitumor agents, *Trends Endocrinol Metab.*, (Dec. 1999), 10(10):383-391.

Schally et al., Hypothalamic hormones and cancer, *Front Neuroendocrinol*, (Oct. 2001), 22(4):248-91.

Schally et al., Antagonists of growth hormone-releasing hormone in oncology, *Combinatorial Chemistry and High Throughput Screening*, (Mar. 1, 2006), 9(3):163-170.

Siejka et al., GH-RH antagonist (MX-4-71) inhibits VEGF secretion and proliferation of murine endothelial cells, *Life Sciences*, (Apr. 18, 2003), 72(22):2473-2479.

Szepeshazi et al., Antagonists of GHRH Decrease Production of GH and IGF-I in MXT Mouse Mammary Cancers and Inhibit Tumor Growth, *Endocrinology*, (Oct. 1, 2001), 142(10):4371-4378.

Szereday et al., Antagonists of growth hormone-releasing hormone inhibit the proliferation of experimental non-small cell lung carcinoma, *Cancer Research*, (Nov. 15, 2003), 63(22): 7913-7919.

Toth et al., New analogs of human growth hormone-releasing hormone (1-29) with high and prolonged antagonististic activity, *Journal of Peptide Research*, (Feb. 1, 1998), 51(2):134-141.

Varga et al., Synthesis and biological evaluation of antagonists of growth hormone-release hormone with high and protracted in vivo activities, *Proceedings of the National Academy of Sciences of USA*, (Jan. 19, 1999), 96(2):692-697.

Varga et al., Increased activity of antagonists of growth hormone-releasing hormone substituted at positions 8, 9, and 10, Proceedings of the National Academy of Sciences of USA, (Feb. 10, 2004), 101(6):1708-1713.

Voskoglou-Nomikos et al., Clinical Predictive Value of the in Vitro Cell Line, Human Xenogroft, and Mouse Allograft Prelinical Cancer Models, *Clinical Cancer Research*, (Sep. 15, 2003), 9:4427-4239.

Zarandi et al., Potent agonists of growth hormone-releasing hormone. Part I., *International Journal of Peptide and Protein Research*, (Mar. 1992), 39(3):211-217.

Zarandi et al., Synthesis and Biological Activities of Highly Potent Antagonists of Growth Hormone-Releasing Hormone, *Proceedings of the National Academy of Sciences of USA*, (Dec. 1, 1994), 91:12298-12302.

http://www.news-medical.net/health/Restenosis-Treatment.aspx, 2 pages.

\* cited by examiner

SEQUENCE LISTING

<160> NUMBER OF SEQ ID NOS: 1

<210> SEQ ID NO 1
<211> LENGTH: 29
<212> TYPE: PRT
<213> ORGANISM: Artificial Sequence
<220> FEATURE:
<223> OTHER INFORMATION: synthetic peptide

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

N- AND C- TERMINAL SUBSTITUTED ANTAGONISTIC ANALOGS OF GH-RH

RELATED APPLICATIONS

This application is a continuation-in-part of PCT Application No. US2009/038351 filed on Mar. 26, 2009, which claims the benefit of U.S. Provisional Application No. 61/040,418 filed on Mar. 28, 2008. This application also claims the benefit of U.S. Provisional Application No. 61/305,737 filed on Feb. 18, 2010. All of the prior applications are incorporated herein by reference in their entirety.

INCORPORATION OF SEQUENCE LISTING

A computer readable form of the sequence listing "12-890626 Sequence Listing_ST25.txt" (743 bytes) submitted via EFS-WEB and created on Oct. 17, 2013, is herein incorporated by reference.

This invention was made in part with Government support from the Medical Research Service of the Veterans Affairs Department. The Government has certain rights in this application.

FIELD OF INVENTION

The present invention relates to novel Synthetic analogs of hGH-RH(1-29)NH$_2$ and hGH-RH(1-30)NH$_2$ that inhibit the release of growth hormone from the pituitary in mammals as well as inhibit the proliferation of human cancers, and inhibit the hyperplastic and benign proliferative disorders of various organs, through a direct effect on the cancerous and non-malignant cells, and to therapeutic compositions containing these novel peptides.

BACKGROUND OF THE INVENTION

Growth hormone-releasing hormone (GH-RH) is a peptide belonging to the secretin/glucagon family of neuroendocrine and gastrointestinal hormones, a family that also includes vasoactive intestinal peptide (VIP), pituitary adenylate cyclase activating peptide (PACAP) and others. Human GH-RH (hGH-RH) peptide is comprised of 44 amino acid residues. The best known site of production of GH-RH is the hypothalamus, but it was found that various peripheral organs also synthesize it. hGH-RH is also produced, sometimes in large quantities, by human malignant tissues (cancers) of diverse origin.

GH-RH exerts various physiological and pathophysiological functions. Hypothalamic GH-RH is an endocrine releasing hormone that, acting through specific GH-RH receptors on the pituitary, regulates the secretion of pituitary growth hormone (GH). The physiological functions of GH-RH in extrapituitary tissues are less clear. However, there is increasing evidence for the role of GH-RH as an autocrine/paracrine growth factor in various cancers. Splice variant (SV) receptors for GH-RH, different from those expressed in the pituitary, have been described in a wide range of human cancers and in some normal peripheral organs. The actions of tumoral autocrine/paracrine GH-RH could be exerted on these receptors. In addition, receptors for VIP and other, as yet unidentified receptors of this family, could all be targets of local GH-RH.

In view of the role of GH-RH as an endocrine regulator of GH release, novel therapeutic strategies, based on the use of agonistic and antagonistic analogs of GH-RH, have been devised for the treatment of various pathological conditions. GH is a polypeptide having 191 amino acids that stimulates the production of different growth factors, e.g. insulin-like growth factor I (IGF-I), and consequently promotes growth of numerous tissues (skeleton, connective tissue, muscle and viscera) and stimulates various physiological activities (raising the synthesis of nucleic acids and proteins, and raising lipolysis, but lowering urea secretion). Release of pituitary GH is under the control of releasing and inhibiting factors secreted by the hypothalamus, the primary releasing factors being GH-RH and ghrelin, and the main inhibiting factor being somatostatin.

GH has been implicated in several diseases. One disease in which GH is involved is acromegaly, in which excessive levels of GH are present. The abnormally enlarged facial and extremity bones, and the cardiovascular symptoms of this disease can be treated by administering a GH-RH antagonist. Further diseases involving GH are diabetic retinopathy and diabetic nephropathy. The damage to the retina and kidneys respectively in these diseases, believed to be due to hypersecretion of GH, results in blindness or reduction in kidney function. This damage can be prevented or slowed by administration of an effective GH-RH antagonist.

In an effort to intervene in these disease and other conditions, some investigators have attempted to control GH and IGF-I levels by using analogs of somatostatin, an inhibitor of GH release. However, somatostatin analogs, if administered alone, do not suppress GH or IGF-I levels to a desired degree. If administered in combination with a GH-RH antagonist, somatostatin analogs will suppress IGF-I levels much better.

However, the main applications of GH-RH antagonists are in the field of cancer (reviewed in Schally A V and Varga J L, Trends Endocrinol Metab 10: 383-391, 1999; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, 6$^{th}$ ed. Hamilton, Ontario: BC. Decker, Inc., 2003, p. 911-926). GH-RH antagonists inhibit the proliferation of malignancies by indirect endocrine mechanisms based on the inhibition of pituitary GH release and resulting in the decrease of serum levels of GH and IGF-I, as well as by direct effects on the tumor tissue.

GH-RH and its tumoral splice variant (SV) receptors are present in human cancers of the lung, prostate, breast, ovary, endometrium, stomach, intestine, pancreas, kidney, and bone (see Halmos G et al, Proc Natl Acad Sci USA 97: 10555-10560, 2000; Rekasi Z et al, Proc Natl Acad Sci USA 97: 10561-10566, 2000; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, 6$^{th}$ ed. Hamilton, Ontario: BC. Decker, Inc., 2003, p. 911-926). Tumoral GH-RH has been shown or it is suspected to act as an autocrine growth factor in these malignancies. Antagonistic analogs of GH-RH can inhibit the stimulatory activity of GH-RH and exert direct antiproliferative effects in vitro on cancer cells, and in vivo on tumors. Direct antiproliferative effects of GH-RH antagonists are exerted on tumoral receptors (binding sites). In addition to the specific tumoral SV receptors for GH-RH, receptors for VIP and other, as yet unidentified receptors of this family, are targets of GH-RH antagonists.

In addition to endocrine inhibitory effects on serum GH and IGF-I, GH-RH antagonists have been found to reduce the autocrine and paracrine production of several tumor growth factors and/or downregulate their receptors. These growth factors include IGF-I, IGF-II, GH, vascular endothelial growth factor (VEGF), and fibroblast growth factor (FGF), Thus, a disruption of the autocrine/paracrine stimulatory loops based on these growth factors contributes to the efficacy of GH-RH antagonists as antitumor agents.

IGF-I and IGF-II are autocrine/paracrine growth factors with potent mitogenic effects on various cancers. IGF-I is also an endocrine growth factor, and elevated levels of serum IGF-I are considered an epidemiological risk factor for the development of prostate cancer, lung cancer, and colorectal cancer. The involvement of IGF-I (somatomedin-C) in breast cancer, prostate cancer, colon cancer, bone tumors and other malignancies is well established. Nevertheless, autocrine/paracrine control of proliferation by IGF-II is also a major factor in many tumors. IGF-I and IGF-II exert their proliferative and anti-apoptotic effects through the common IGF-I receptor. The receptors for IGF-I are present in primary human breast cancers, prostate cancers, lung cancers, colon cancers, brain tumors, pancreatic cancers, and in renal cell carcinomas. In several experimental cancers, such as those of the bone, lung, prostate, kidney, breast, ovary, intestine, pancreas, and brain, treatment with GH-RH antagonists produces a reduction in IGF-I and/or IGF-II levels, concomitant to inhibition of tumor growth (reviewed in Schally A V and Varga J L, Trends Endocrinol Metab 10: 383-391, 1999; Schally A V et al, Frontiers Neuroendocrinol 22: 248-291, 2001; Schally A V and Comaru-Schally A M, in: Kufe D W, Pollock R E, Weichselbaum R R, Bast Jr. R C, Gansler T S, Holland J F, Frei III E, Eds. Cancer Medicine, $6^{th}$ ed. Hamilton, Ontario: BC. Decker, Inc., 2003, p. 911-926). In some cases, the expression of IGF-I receptors was also decreased by GH-RH antagonists. Thus the disruption of endocrine and autocrine/paracrine stimulatory loops dependent on IGF-I and IGF-II contributes to the antitumor effect of GH-RH antagonists.

In MXT breast cancer model, treatment with GH-RH antagonists inhibited tumor growth, reduced the mRNA level for GH and the concentration of GH peptide in tumors, and inhibited the mRNA expression for GH receptors (Szepeshazi K et al, Endocrinology 142: 4371-4378, 2001). GH was shown to act as a growth factor for MXT murine mammary carcinoma cells, MCF-7 human breast cancer cells and other tumor cell lines. Thus the inhibitory activity of GH-RH antagonists on local and serum GH levels contributes to their antitumor effect.

GH-RH antagonists have been shown to inhibit the mRNA levels and protein concentrations of VEGF in human androgen-sensitive and androgen-independent prostate cancer models (Letsch M et al, Proc Natl Acad Sci USA 100: 1250-1255, 2003; Plonowski A et al, Prostate 52: 173-182, 2002) and this phenomenon contributes to their antitumor effect, since VEGF plays an important stimulatory role in the neovascularization and growth of various tumors. Moreover, it was found that a GH-RH antagonist inhibited the VEGF secretion and proliferation of normal murine endothelial cells, apparently through a direct effect on these cells in vitro (Siejka A et al, Life Sci 72: 2473-2479, 2003).

Scientists have investigated various modifications of GH-RH to elucidate the relationship of the structure of GH-RH to its activity on the pituitary receptors, in an effort to provide synthetic congeners with improved agonistic or antagonistic properties. Thus, it was early established that GH-RH fragment comprising residues 1 to 29, or GH-RH(1-29), is the minimum sequence necessary for biological activity on the pituitary. This fragment retains 50% or more of the potency of native GH-RH. Subsequently, many synthetic analogs of GH-RH, based on the structure of hGH-RH(1-29)NH$_2$ (SEQ ID NO: 1) peptide, were prepared. hGH-RH(1-29)NH$_2$ (SEQ ID NO: 1) has the following amino acid sequence:

Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-NH$_2$ (SEQ ID NO: 1)

A considerable number of patents and articles in the open literature disclose analogs of GH-RH which either act as agonists of GH-RH (i.e. act to stimulate the release of GH) or as antagonists of GH-RH (i.e. act to inhibit the release of GH) on the pituitary. Most of these peptides are derived from the GH-RH(1-29) peptide sequence, with specific structural modifications which account for their enhanced agonistic or antagonistic properties on the pituitary receptors. However, apart from a few exceptions, it is not known how these analogs would behave on cancer cells that express GH-RH receptors different from those found in the pituitary. Only a few published scientific studies tried to elucidate the structure-activity relationships and characterize the direct antagonistic (or agonistic) effects of GH-RH analogs on cancer cells and tumors (see Rekasi Z et al, Endocrinology 141: 2120-2128, 2000; Halmos G et al, Proc Natl Acad Sci USA 97: 10555-10560, 2000; Rekasi Z et al, Proc Natl Acad Sci USA 97: 10561-10566, 2000; Kiaris H et al, Proc Natl Acad Sci USA 99: 196-200, 2002), and no issued patents have dealt with this issue so far. Consequently, very little is known about the structural features in GH-RH analogs required for a direct antagonistic action on tumor cells.

The first described GH-RH antagonist, [Ac-Tyr$^1$, D-Arg$^2$]hGH-RH(1-29)NH$_2$, which is generally termed as the "standard antagonist" in the literature, was found to prevent the activation of rat anterior pituitary adenylate cyclase by hGH-RH(1-29)NH$_2$ (SEQ ID NO: 1). The same peptide blocked the action of GH-RH on its receptors in the pituitary and hypothalamus, and inhibited the pulsatile growth hormone secretion. The standard antagonist was also evaluated clinically (Ocampo-Lim B et al, J Clin Endocrinol Metab 81: 4396-4399, 1996; Jaffe C A et al, J Clin Endocrinol Metab 82: 634-637, 1997). Large doses of this antagonist (400 µg/kg) eliminated nocturnal GH secretion in normal subjects and inhibited the response to GH-RH. The standard GH-RH antagonist also reduced GH levels in a patient with acromegaly. However, for clinical use, much more potent antagonists of GH-RH are required.

The inventions mentioned below disclose GH-RH analogs with antagonistic or agonistic properties on the pituitary receptors for GH-RH. However it was not reported and not investigated whether these analogs could exert direct effects on tumor cells. U.S. Pat. No. 4,659,693 discloses GH-RH antagonistic analogs which contain certain N,N'-dialkyl-omega-guanidino alpha-amino acyl residues in position 2 of the GH-RH(1-29) sequence. Published application WO 91/16923 reviews earlier attempts to alter the secondary structure of hGH-RH by modifying its amino acid sequence. These earlier attempts include: replacing Tyr$^1$, Ala$^2$, Asp$^3$ or Asn$^8$ with their D-isomers; replacing Asn$^8$ with L- or D-Ser, D-Arg, Asn, Thr, Gln or D-Lys; replacing Ser$^9$ with Ala to enhance amphiphilicity of the region; and replacing Gly$^{15}$ with Ala or Aib. When R$^2$ in the analogs is D-Arg, and R$^8$, R$^9$, and R$^{15}$ are substituted as indicated above, antagonistic activity is said to result. These antagonistic peptides are said to be suitable for administration as pharmaceutical compositions to treat conditions associated with excessive levels of GH, e.g., acromegaly.

The antagonistic activity of the hGH-RH analogue "[Ser$^9$-psi[CH$_2$—NH]-Tyr$^{10}$]hGH-RH(1-29)" of U.S. Pat. No. 5,084,555 was said to result from the pseudopeptide bond (i.e., a peptide bond reduced to a [CH$_2$—NH] linkage) between the R$^9$ and R$^{10}$ residues. However, the antagonistic properties of [Ser$^9$-psi[CH$_2$—NH]-Tyr$^{10}$]hGH-RH(1-29)

were said to be inferior to the standard antagonist, [Ac-Tyr¹, D-Arg²]hGH-RH(1-29)-NH₂. U.S. Pat. No. 5,550,212, U.S. Pat. No. 5,942,489, and U.S. Pat. No. 6,057,422, disclose analogs of hGH-RH(1-29)NH₂ (SEQ ID NO: 1) said to have enhanced antagonistic properties and prolonged duration of action regarding the inhibition of GH-RH-evoked GH release. These properties are believed to result from replacement of various amino acids and acylation with aromatic or nonpolar acids at the N-terminus of GH-RH(1-29)NH₂. The tumor inhibitory properties of antagonists featured in U.S. Pat. No. 5,942,489 and U.S. Pat. No. 6,057,422 have been demonstrated by using nude mice bearing xenografts of experimental human cancer models. It is noted that in U.S. Pat. No. 5,550,212, and in U.S. Pat. No. 5,942,489, R⁹ is always Ser, while R¹¹ and R²⁰ can be either Arg, D-Arg, or Cit. In the case of U.S. Pat. No. 6,057,422, R⁹ can be either Arg, Har, Lys, Orn, D-Arg, D-Har, D-Lys, D-Orn, Cit, Nle, Tyr(Me), Ser, Ala, or Aib, while R¹¹ and R²⁰ are always Arg.

SUMMARY OF THE INVENTION

Figure 1:
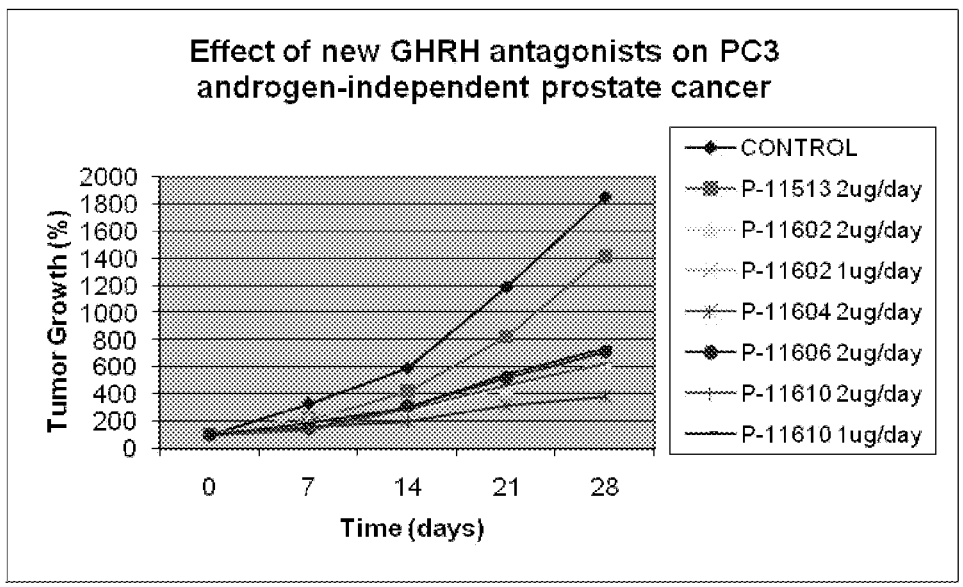
FIG. 1 is a plot of tumor growth in % against time in days of the effect of certain novel GHRH antagonists on PC3 androgen-independent prostate cancer.
Figure 2:
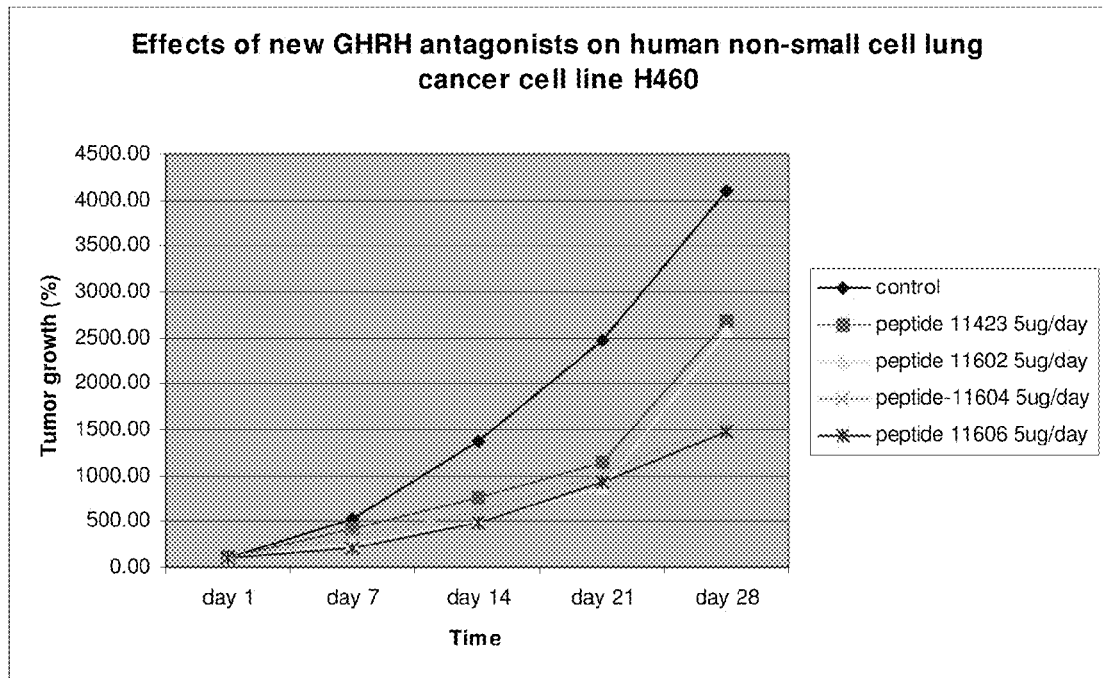
FIG. 2 is a plot of tumor growth in % against time in days of the effect of certain novel GHRH antagonists on human non-small cell lung cancer cell line H-460.

There is provided a novel series of synthetic analogs of hGH-RH(1-29)NH₂ (SEQ ID NO: 1) and hGH-RH(1-30)NH₂. These analogs inhibit the release of growth hormone from the pituitary in mammals as well as inhibit the proliferation of human cancers, and inhibit the hyperplastic and benign proliferative disorders of various organs, through a direct effect on the cancerous and non-malignant cells. The stronger inhibitory potencies of the new analogs, as compared to previously described ones, results from replacement of various amino acids.

The invention principally relates to peptides comprising the formulae: A peptide selected from the group having the formulae:

[A⁰-Tyr¹-D-Arg²,A⁴,A⁶,A⁸,Har⁹,Tyr(Me)¹⁰,A¹¹,A¹²,
Abu¹⁵,A¹⁷,A²⁰,A²¹,Nle²⁷,D-Arg²⁸,A²⁹-A³⁰-A³¹]
hGH-RH(1-29)NH₂ wherein
A⁰ is PhAc, N-Me-Aib, Dca, Ac-Ada, Fer, Ac-Amc, Me-NH-Sub, PhAc-Ada, Ac-Ada-D-Phe, Ac-Ada-Phe, Dca-Ada, Dca-Amc, Nac-Ada, Ada-Ada, or CH₃—(CH₂)₁₀—CO-Ada, A⁴ is Ala or Me-Ala
A⁶ is Cpa or Phe(F)₅
A⁸ is Ala, Pal, or Me-Ala
A¹¹ is H is or Arg
A¹² is Lys, Lys(0-11), Lys(Me)₂ or Orn,
A¹⁷ is Leu or Glu
A²⁰ is Har or His
A²¹ is -Lys, Lys(Me)₂ or Orn
A²⁹ is Har, Arg or Agm
A³⁰ is absent, β-Ala, Amc, Apa, Ada, AE₂A, AE₄P, ε-Lys (α-NH₂) or Agm
A³¹ is absent, Lys(Oct) or Ahx
provided that where A⁰ is PhAc, A¹² and A²¹ are both other than Orn and A³⁰ is not absent, and
[A⁰-Tyr¹, D-Arg², Cpa⁶, Ala⁸, His⁹, Tyr(Et)¹⁰, His¹¹, Orn¹², Abu¹⁵, His²⁰, Orn²¹, Nle²⁷, D-Arg²⁸, Har²⁹-Ada³⁰] hGH-RH(1-29)NH₂ wherein A⁰ is Oct or Ac-Ada,
and pharmaceutically acceptable salts thereof.

The invention principally relates to peptides comprising the formulae: A peptide selected from the group having the formulae:

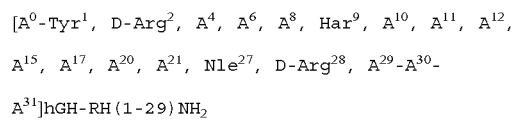

[A⁰-Tyr¹, D-Arg², A⁴, A⁶, A⁸, Har⁹, A¹⁰, A¹¹, A¹²,
A¹⁵, A¹⁷, A²⁰, A²¹, Nle²⁷, D-Arg²⁸, A²⁹-A³⁰-
A³¹]hGH-RH(1-29)NH₂ wherein
A⁰ is PhAc, Nac, Oct, N-Me-Aib, Dca, Ac-Ada, Fer, Ac-Amc, Me-NH-Sub, PhAc-Ada, Ac-Ada-D-Phe, Ac-Ada-Phe, Dca-Ada, Dca-Amc, Nac-Ada, Ada-Ada, or CH₃—(CH₂)₁₀—CO-Ada,
A⁴ is Ala or Me-Ala
A⁶ is Cpa or Phe(F)₅
A⁸ is Ala, Pal, Dip, or Me-Ala
A is Tyr (Alk) where Alk is Me or Et,
A¹¹ is His or Arg
A¹² is Lys, Lys(0-11), Lys(Me)₂ or Orn,
A¹⁵ is Abu or Orn,
A¹⁷ is Leu or Glu
A²⁰ is Har or His
A²¹ is -Lys, Lys(Me)₂ or Orn
A²⁹ is Har, Arg or Agm
A³⁰ is absent, β-Ala, Amc, Apa, Ada, AE₂A, AE₄P, ε-Lys(α-NH₂) or Agm
A³¹ is absent, Lys(Oct) or Ahx
provided that where A⁰ is PhAc, Nac, or Oct, A³⁰ is not absent, and pharmaceutically acceptable salts thereof.

Suitably, [A⁰-Tyr¹, D-Arg², Ala⁴, A⁶, A⁸, Har⁹, A¹⁰, His¹¹, A¹², Abu¹⁵, A¹⁷, His²⁰, A²¹, Nle²⁷, D-Arg²⁸, Har²⁹-A³⁰] hGH-RH(1-29)NH₂
wherein
A⁰ is PhAc, Dca, Ac-Ada, Fer, Ac-Amc, PhAc-Ada, Ac-Ada-D-Phe, Dca-Ada, Dca-Amc, Nac, Oct, or CH₃—(CH₂)₁₀—CO-Ada
A⁶ is Cpa or Phe(F)₅
A⁸ is Ala or Me-Ala
A¹⁰ is Tyr (Alk) where Alk is Me or Et
A¹² is Lys, or Orn,
A¹⁷ is Leu or Glu
A²¹ is -Lys, or Orn
A³⁰ is absent, Amc, Apa, Ada, AE₂A, or Agm
provided that where A⁰ is PhAc, Nac, or Oct, A³⁰ is not absent and pharmaceutically acceptable salts thereof.

Most suitably, peptides listed in the immediately foregoing paragraph wherein A⁰ is Dca, Ac-Ada, Ac-Amc, PhAc-Ada, Dca-Ada, Nac, Oct, or CH₃—(CH₂)₁₀—CO-Ada and A³⁰ is Agm, Ada, or absent.

It is noted that the amino acid residues from 30 through 44 of the native GH-RH molecule do not appear to be essential to activity; nor does their identity appear to be critical. Therefore, it appears that the addition of some or all of these further amino acid residues to the C-terminus of the hGH-RH(1-29) NH₂ (SEQ ID NO: 1) and hGH-RH(1-30)NH₂ analogs of the present invention will not affect the efficacy of these analogs as GH-RH antagonists.

If some or all of these amino acids were added to the C-terminus of the hGH-RH(1-29)NH₂ (SEQ ID NO: 1) analogs, the added amino acid residues could be the same as residues 30 through 44 in the native hGH-RH sequence or reasonable equivalents.

Synthetic Methods.

The synthetic peptides are synthesized by a suitable method such as by exclusive solid phase techniques, by partial solid-phase techniques, by fragment condensation or by classical solution phase synthesis. When the analogs of this invention are synthesized by solid-phase method, the C-terminus residue (here, $A^{29}$ or $A^{30}$) is appropriately linked (anchored) to an inert solid support (resin) while bearing protecting groups for its alpha or omega amino group (and, where appropriate, for its side chain functional group). After completion of this step, the alpha (or omega) amino protecting group is removed from the anchored amino acid residue and the next amino acid residue, $A^{28}$ or $A^{29}$ respectively, is added having its alpha amino group (as well as any appropriate side chain functional group) suitably protected, and so forth. The N-terminus protecting groups are removed after each residue is added, but the side chain protecting groups are not yet removed. After all the desired amino acids have been linked in the proper sequence, the peptide is cleaved from the support and freed from all side chain protecting group(s) under conditions that are minimally destructive towards residues in the sequence. This is be followed by a careful purification and scrupulous characterization of the synthetic product, so as to ensure that the desired structure is indeed the one obtained.

It is particularly preferred to protect the alpha amino function (or the omega amino function, where applicable) of the amino acids during the coupling step with an acid or base sensitive protecting group. Such protecting groups should have the properties of being stable in the conditions of peptide linkage formation, while being readily removable without destruction of the growing peptide chain and without racemization of any of the chiral centers contained therein. Suitable alpha and omega amino protecting groups are Boc and Fmoc.

Medical Applications

The hGH-RH antagonist peptides, or salts of these peptides, may be formulated in pharmaceutical dosage forms containing effective amounts thereof and administered to humans or animals for therapeutic or diagnostic purposes. The peptides may be used to suppress GH levels and to treat conditions associated with excessive levels of GH, e.g., diabetic retinopathy and nephropathy, and acromegaly. Also provided are methods for treating these diseases by administration of a composition of the invention to an individual needing such treatment. The main uses of GH-RH antagonists are, however, in the field of cancer, for example human cancers of the lung, prostate, breast, ovary, endometrium, stomach, colon, pancreas, kidney, bone, and brain where the receptors for GH-RH, IGF-I/IGF-II, or GH are present, and that depend on stimulation by growth factors such as GH-RH, IGF-I, IGF-II, GH, VEGF, or FGF.

DETAILED DESCRIPTION OF THE PREFERRED EMBODIMENTS

A. Abbreviations

The nomenclature used to define the peptides is that specified by the IUPAC-IUB Commission on Biochemical Nomenclature wherein, in accordance with conventional representation, the amino group at the N-terminus appears to the left and the carboxyl group at the C-terminus appears to the right. The term "natural amino acid" as used herein means one of the common, naturally occurring L-amino acids found in naturally occurring proteins: Gly, Ala, Val, Leu, Ile, Ser, Thr, Lys, Arg, Asp, Asn, Glu, Gln, Cys, Met, Phe, Tyr, Pro, Trp and His. When the natural amino acid residue has isomeric forms, it is the L-form of the amino acid that is represented herein unless otherwise expressly indicated.

Non-coded amino acids, or amino acid analogues, are also incorporated into the GH-RH antagonists. ("Non-coded" amino acids are those amino acids which are not among the approximately 20 natural amino acids found in naturally occurring proteins). When these non-coded amino acids, or amino acid analogues, have isomeric forms, it is the L-form of the amino acid that is represented unless otherwise expressly indicated.

Abbreviations used herein are:
Abu alpha-aminobutyric acid
Ac acetyl
AcOH acetic acid
$Ac_2O$ acetic anhydride
Ada 12-aminododecanoyl
$AE_2A$ 8-amino-3,6-dioxaoctanoyl
$AE_4P$ 15-amino-4,7,10,13-tetraoxapentadecanoyl
Agm agmatine
Ahx 6-Aminohexanoyl
Amc 8-Aminocaprylyl
Apa 5-Aminopentanoyl
Aib alpha-aminoisobutyroyl
All allyl
Alloc allyloxycarbonyl
Amp para-amidino-phenylalanine
Bpa para-benzoyl-phenylalanine
Boc tert-butyloxycarbonyl
Bom benzyloxymethyl
2BrZ 2-bromo-benzyloxycarbonyl
Bzl benzyl
Cha cyclohexylalanine
Chg cyclohexylglycine
cHx cyclohexyl
Cit citrulline (2-amino-5-ureidovaleroyl
2ClZ 2-chloro-benzyloxycarbonyl
Cpa para-chlorophenylalanine
Dat des-amino-tyrosine
Dca Dichloroacetyl
DCM dichloromethane
DIC N,$N^1$-diisopropylcarbodiimide
DIEA diisopropylethylamine
Dip (3,3-diphenyl)alanine
DMF dimethylformamide
Et ethyl
Fer feruyl
FGF fibroblast growth factor
Fm fluorenylmethyl
Fmoc fluorenylmethoxycarbonyl
For formyl
GH growth hormone
GH-RH GH releasing hormone
Gup para-guanidino-phenylalanine
Har homoarginine
HBTU 2-(1H-Benzotriazol-1-yl)-1,1,3,3-Tetramethyluronium hexafluorophosphate
Hca hydrocinnamoyl
Hca-OH hydrocinnamic acid
hGH-RH human GH-RH
HOBt 1-hydroxybenzotriazole
HPLC high performance liquid chromatography
Ibu isobutyryl
IndAc indole-3-acetyl
Ipa indole-3-propionyl
Lys(0-11) Lys($A^0$-$A^1$-$A^2$-$A^3$-$A^4$-$A^5$-$A^6$-$A^7$-$A^8$-$A^9$-$A^{10}$-$A^{11}$-)

ε-Lys(α-NH$_2$) a Lys residue, the ε-amino group of which is acylated by the carbonyl group of an N-terminally located amino acid; the α-amino group of the Lys residue is free para-methylbenzhydrylamine
MBHA para-methylbenzhydrylamine
Me methyl
MeOH methanol
MeCN acetonitrile
Nac naphthylacetyl
Nal naphthylalanine
Nle norleucine
NMM N-methylmorpholine
Npr naphthylpropionyl
Oct octanoyl
Orn ornithine
Peg pegyl
Pal pyridylalanine
PAM phenylacetamidomethyl
Ph Phenyl
PhAc phenylacetyl
PhAc—OH Phenylacetyl
Phe(F)$_5$ pentafluoro-phenylalanine
Phe(pCl) para-chloro-phenylalanine
Phe(pNH$_2$) para-amino-phenylalanine
Phe(pNO$_2$) para-nitro-phenylalanine
rGH-RH rat GH-RH
RP-HPLC reversed phase HPLC
Sub suberyl
SPA para-sulfonyl-phenoxyacetyl
TFA trifluoroacetic acid
Tos para-toluenesulfonyl
Tpi 1,2,3,4-tetrahydronorharman-3-carboxylic acid
Tyr(Me) O-methyl-tyrosine
Tyr(Et) O-ethyl-tyrosine
z benzyloxycarbonyl B. The GH-RH Analogs The hGH-RH analogs of the present invention were designed to increase the antagonistic effects at the pituitary level, and/or at the tumoral level.

Particularly preferred are the peptides of the structure shown in Table A below:

TABLE A

| | |
|---|---|
| P-1109 | [PhAc$^0$-Tyr$^1$, D-Arg$^2$, Cpa$^6$, Ala$^8$, Har$^9$, Tyr(Me)$^{10}$, His$^{11}$, Abu$^{15}$, Glu$^{17}$, His$^{20}$, Nle$^{27}$, D-Arg$^{28}$, Har$^{29}$]hGH-RH(1-29)NH$_2$ |
| P-1111 | [PhAc$^0$-Tyr$^1$, D-Arg$^2$, (Me-Ala)$^4$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-1113 | [PhAc$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-1115 | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hGH-RH(1-29)NH$_2$ |
| P-1117 | [PhAc$^0$-Tyr$^1$, D-Arg$^2$, Cpa$^6$, Ala$^8$, Har$^9$, Tyr(Me)$^{10}$, His$^{11}$, (Lys(Me)$_2$)$^{12}$, Abu$^{15}$, His$^{20}$, (Lys(Me)$_2$)$^{21}$, Nle$^{27}$, D-Arg$^{28}$, Har$^{29}$]hGH-RH(1-29)NH$_2$ |
| P-11107 | [(N—Me-Aib)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11111 | [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11113 | [Fer$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11115 | [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11117 | [(PhAc-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11119 | [(Ac-Ada-D-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11121 | [(Ac-Ada-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11123 | [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11125 | [(CH$_3$-(CH$_2$)$_{10}$-CO-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11207 | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$ |
| P-11209 | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Apa$^{30}$]hGH-RH(1-29)NH$_2$ |
| P-11211 | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$ |
| P-11213 | [Oct$^0$-Tyr$^1$, D-Arg$^2$, Cpa$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11215 | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$]hGH-RH(1-29)NH$_2$ |
| P-11307 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Amc$^{30}$]hGH-RH(1-29)NH$_2$ |
| P-11309 | [(Me—NH-Sub)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$ |
| P-11311 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Agm$^{29}$]hGH-RH(1-29)NH$_2$ |
| P-11313 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Agm$^{30}$]hGH-RH(1-29)NH$_2$ |
| P-11315 | [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$ |
| P-11317 | [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$ |
| P-11319 | [(Ac-Ada)$^0$-Tyr$^1$, D-Arg$^2$, Cpa$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |

TABLE A-continued

| | |
|---|---|
| P-11321 | [(Ac-Ada)⁰-Tyr¹, D-Arg², Cpa⁶, Ala⁸, Har⁹, Tyr(Me)¹⁰, His¹¹, Abu¹⁵, His²⁰, Nle²⁷, D-Arg²⁸, Arg²⁹-Ada³⁰]hGH-RH(1-29)NH₂ |
| P-11407 | [(Ac-Amc)⁰-Tyr¹, D-Arg², (Me-Ala)⁴, Cpa⁶, Ala⁸, Har⁹, Tyr(Me)¹⁰, His¹¹, Abu¹⁵, His²⁰, Nle²⁷, D-Arg²⁸, Har²⁹]hGH-RH(1-29)NH₂ |
| P-11408 | [(Ac-Amc)⁰-Tyr¹, D-Arg², Cpa⁶, (Me-Ala)⁸, Har⁹, Tyr(Me)¹⁰, His¹¹, Abu¹⁵, His²⁰, Nle²⁷, D-Arg²⁸, Har²⁹]hGH-RH(1-29)NH₂ |
| P-11409 | [(Ac-Amc)⁰-Tyr¹, D-Arg², (Me-Ala)⁴, Cpa⁶, (Me-Ala)⁸, Har⁹, Tyr(Me)¹⁰, His¹¹, Abu¹⁵, His²⁰, Nle²⁷, D-Arg²⁸, Har²⁹]hGH-RH(1-29)NH₂ |
| P-11411 | [PhAc⁰-Tyr¹, D-Arg², Cpa⁶, (Me-Ala)⁸, Har⁹, Tyr(Me)¹⁰, His¹¹, Abu¹⁵, His²⁰, Nle²⁷, D-Arg²⁸, Har²⁹-Amc³⁰]hGH-RH(1-29)NH₂ |
| P-11413 | [PhAc⁰-Tyr¹, D-Arg², Cpa⁶, 3-Pal⁸, Har⁹, Tyr(Me)¹⁰, His¹¹, Abu¹⁵, His²⁰, Nle²⁷, D-Arg²⁸, Har²⁹-Amc³⁰]hGH-RH(1-29)NH₂ |
| P-11415 | [(Ac-Amc)⁰-Tyr¹, D-Arg², Cpa⁶, (Me-Ala)⁸, Har⁹, Tyr(Me)¹⁰, His¹¹, Abu¹⁵, His²⁰, Nle²⁷, D-Arg²⁸, Har²⁹-Agm³⁰]hGH-RH(1-29) |
| P-11417 | [(Ac-Amc)⁰-Tyr¹, D-Arg², Cpa⁶, (Me-Ala)⁸, Har⁹, Tyr(Me)¹⁰, His¹¹, Abu¹⁵, His²⁰, Nle²⁷, D-Arg²⁸, Har²⁹-Amc³⁰]hGH-RH(1-29)NH₂ |
| P-11419 | [PhAc⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11421 | [(N—Me-Aib)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11423 | [PhAc⁰-Tyr¹, D-Arg², Cpa⁶, Dip⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11425 | [PhAc⁰-Tyr¹, D-Arg², Cpa⁶, Ala⁸, Har⁹, Tyr(Me)¹⁰, His¹¹, Lys(PhAc-Tyr-D-Arg-Asp-Ala-Ile-Cpa-Thr-Ala-Har-Tyr(Me)-His-)¹², Abu¹⁵, His²⁰, Orn²¹, Nle²⁷, D-Arg²⁸, Har²⁹]hGH-RH(1-29)NH₂, where (0-11) denotes the following peptide sequence: PhAc-Tyr-D-Arg-Asp-Ala-Ile-Cpa-Thr-Ala-Har-Tyr(Me)-His-; the C-terminal carbonyl group of the (0-11) peptide sequence forms an amide bond with the epsilon amino group of Lys¹². |
| P-11427 | [(N—Me-Aib)⁰-Tyr¹, D-Arg², Cpa⁶, Ala⁸, Har⁹, Tyr(Me)¹⁰, His¹¹, Lys((N—Me-Aib)-Tyr-D-Arg-Asp-Ala-Ile-Cpa-Thr-Ala-Har-Tyr(Me)-His-)¹², Abu¹⁵, His²⁰, Orn²¹, Nle²⁷, D-Arg²⁸, Har²⁹]hGH-RH(1-29)NH₂, where (0-11) denotes the following peptide sequence: (N—Me-Aib)-Tyr-D-Arg-Asp-Ala-Ile-Cpa-Thr-Ala-Har-Tyr(Me)-His-; the C-terminal carbonyl group of the (0-11) peptide sequence forms an amide bond with the epsilon amino group of Lys¹². |
| P-11429 | [PhAc⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-β-Ala³⁰-Lys(Oct)³¹]-hGH-RH(1-29)NH₂ |
| P-11431 | [(N—Me-Aib)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-β-Ala³⁰-Lys(Oct)³¹]hGH-RH(1-29)NH₂ |
| P-11433 | [Nac⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11435 | [(Ac-Ada)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹]hGH-RH(1-29)NH₂ |
| P-11437 | [(Dca-Ada)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹]hGH-RH(1-29)NH₂ |
| P-11439 | [(Ac-Ada)⁰-Tyr¹, D-Arg², Cpa⁶, Ala⁸, Har⁹, Tyr(Me)¹⁰, His¹¹, Abu¹⁵, His²⁰, (Lys(Me)₂)²¹, Nle²⁷, D-Arg²⁸, Har²⁹]hGH-RH(1-29)NH₂ |
| P-11441 | [(Ac-Ada)⁰-Tyr¹, D-Arg², Cpa⁶, Ala⁸, Har⁹, Tyr(Me)¹⁰, His¹¹, (Lys(Me)₂)¹², Abu¹⁵, His²⁰, (Lys(Me)₂)²¹, Nle²⁷, D-Arg²⁸, Har²⁹]hGH-RH(1-29)NH₂ |
| P-11443 | [(Dca-Ada)⁰-Tyr¹, D-Arg², Cpa⁶, Ala⁸, Har⁹, Tyr(Me)¹⁰, His¹¹, Abu¹⁵, His²⁰, (Lys(Me)₂)²¹, Nle²⁷, D-Arg²⁸, Har²⁹]hGH-RH(1-29)NH₂ |
| P-11445 | [(Dca-Ada)⁰-Tyr¹, D-Arg², Cpa⁶, Ala⁸, Har⁹, Tyr(Me)¹⁰, His¹¹, (Lys(Me)₂)¹², Abu¹⁵, His²⁰, (Lys(Me)₂)²¹, Nle²⁷, D-Arg²⁸, Har²⁹]hGH-RH(1-29)NH₂ |
| P-11447 | [PhAc⁰-Tyr¹, D-Arg², Cpa⁶, Ala⁸, Har⁹, Tyr(Me)¹⁰, His¹¹, Orn¹², Abu¹⁵, Har²⁰, Orn²¹, Nle²⁷, D-Arg²⁸, Har²⁹]hGH-RH(1-29)NH₂ |
| P-11449 | [(Ac-Ada)⁰-Tyr¹, D-Arg², Cpa⁶, Ala⁸, Har⁹, Tyr(Me)¹⁰, His¹¹, Orn¹², Abu¹⁵, Har²⁰, Orn²¹, Nle²⁷, D-Arg²⁸, Har²⁹]hGH-RH(1-29)NH₂ |
| P-11451 | [(Nac-Ada)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11453 | [(Dca-Ada)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11455 | [(Ac-Ada)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-AE₂A³⁰]hGH-RH(1-29)NH₂ |
| P-11457 | [PhAc⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹-Ada³⁰]hGH-RH(1-29)NH₂ |
| P-11459 | [(PhAc-Ada)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹]hGH-RH(1-29)NH₂ |
| P-11461 | [(Ac-Ada-Phe)⁰-Tyr¹, D-Arg², Cpa⁶, Ala⁸, Har⁹, Tyr(Me)¹⁰, His¹¹, Orn¹², Abu¹⁵, His²⁰, Orn²¹, Nle²⁷, D-Arg²⁸, Har²⁹]hGH-RH(1-29)NH₂ |
| P-11463 | [PhAc⁰-Tyr¹, D-Arg², Cpa⁶, Ala⁸, Har⁹, Tyr(Me)¹⁰, His¹¹, Orn¹², Abu¹⁵, His²⁰, Nle²⁷, D-Arg²⁸, Har²⁹-Amc³⁰]hGH-RH(1-29)NH₂ |
| P-11465 | [PhAc⁰-Tyr¹, D-Arg², Cpa⁶, Ala⁸, Har⁹, Tyr(Me)¹⁰, His¹¹, Abu¹⁵, His²⁰, Orn²¹, Nle²⁷, D-Arg²⁸, Har²⁹-Ada³⁰]hGH-RH(1-29)NH₂ |
| P-11467 | [(Ada-Ada)⁰-Tyr¹, D-Arg², Cpa⁶, Ala⁸, Har⁹, Tyr(Me)¹⁰, His¹¹, Abu¹⁵, His²⁰, Orn²¹, Nle²⁷, D-Arg²⁸, Har²⁹-Ada³⁰]hGH-RH(1-29)NH₂ |
| P-11469 | [(Ac-Ada)⁰-Tyr¹, D-Arg², Cpa⁶, Ala⁸, Har⁹, Tyr(Me)¹⁰, His¹¹, Abu¹⁵, His²⁰, Orn²¹, Nle²⁷, D-Arg²⁸, Har²⁹-Ada³⁰]hGH-RH(1-29)NH₂ |

TABLE A-continued

| | |
|---|---|
| P-11471 | [(Ac-Ada)$^0$-Tyr$^1$, D-Arg$^2$, Cpa$^6$, Ala$^8$, Har$^9$, Tyr(Me)$^{10}$, His$^{11}$, Lys((Ac-Ada)-Tyr-D-Arg-Asp-Ala-Ile-Cpa-Thr-Ala-Har-Tyr(Me)-His-)$^{12}$, Abu$^{15}$, His$^{20}$, Orn$^{21}$, Nle$^{27}$, D-Arg$^{28}$, Har$^{29}$]hGH-RH(1-29)NH$_2$ where (0-11) denotes the following peptide sequence: PhAc-Tyr-D-Arg-Asp-Ala-Ile-Cpa-Thr-Ala-Har-Tyr(Me)-His-; the C-terminal carbonyl group of the (0-11) peptide sequence forms an amide bond with the epsilon amino group of Lys$^{12}$. |
| P-11473 | [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11475 | [(Ac-Ada-D-Phe)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11477 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, His$^{20}$, Nle$^{27}$, D-Arg$^{28}$, Har$^{29}$]hGH-RH(1-29)NH$_2$ |
| P-11479 | [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11481 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-ε-Lys(α-NH$_2$)$^{30}$-Ahx$^{31}$]hGH-RH(1-29)NH$_2$ |
| P-11483 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_4$P$^{30}$]hGH-RH(1-29)NH$_2$ |
| P-11485 | [(CH$_3$—(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11487 | [(CH$_3$—(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11491 | [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11497 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11499 | [PhAc$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11501 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$ |
| P-11503 | [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$ |
| P-11513 | [Dca$^0$-Tyr$^1$, D-Arg$^2$, Cpa$^6$, Ala$^8$, Har$^9$, Tyr(Me)$^{10}$, His$^{11}$, Orn$^{12}$, Har$^{20}$, Orn$^{21}$, Nle$^{27}$, D-Arg$^{28}$, Har$^{29}$]hGH-RH(1-29)NH$_2$ |
| P-11515 | [(Dca-Ada)$^0$-Tyr$^1$, D-Arg$^2$, Cpa$^6$, Ala$^8$, Har$^9$, Tyr(Me)$^{10}$, His$^{11}$, Lys(0-11), Abu$^{15}$, His$^{20}$, Orn$^{21}$, Nle$^{27}$, D-Arg$^{28}$, Har$^{29}$]hGH-RH(1-29)NH$_2$, where (0-11) denotes the following peptide sequence: PhAc-Tyr-D-Arg-Asp-Ala-Ile-Cpa-Thr-Ala-Har-Tyr(Me)-His-; the C-terminal carbonyl group of the (0-11) peptide sequence forms an amide bond with the epsilon amino group of Lys$^{12}$ |
| P-11521 | [(Dca-Amc)$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11523 | [PhAc$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, Glu$^{17}$, His$^{20}$, Orn$^{21}$, Nle$^{27}$, D-Arg$^{28}$, Har$^{29}$-Ada$^{30}$]hGH-RH(1-29)NH$_2$ |
| P-11525 | [PhAc$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11601 | [(CH$_3$—(CH$_2$)$_{10}$-CO-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11602 | [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11603 | [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11604 | [(PhAc-Ada)$^0$-Tyr$^1$, D-Arg$^2$, (Phe(F)$_5$)$^6$, Ala$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-29)NH$_2$ |
| P-11606 | [(PhAc-Ada)$^0$-Tyr', D-Arg$^2$, (Phe(F)$_5$)$^6$, (Me-Ala)$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-29)NH$_2$ |
| P-11610 | [PhAc$^0$-Tyr$^1$, D-Arg$^2$, Cpa$^6$, Ala$^8$, Har$^9$, (Phe(F)$_5$)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11611 | [(Ac-Amc)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11612 | [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11620 | [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$]hGH-RH(1-29)NH$_2$ |
| P-11621 | [(Me—NH-Sub)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$ |
| P-11630 | [(Ac-Ada)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$ |
| P-11701 | [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, Orn$^{21}$, Nle$^{27}$, D-Arg$^{28}$, Har$^{29}$-AE$_4$P$^{30}$]hGH-RH(1-29)NH$_2$ |
| P-11702 | [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$-AE$_4$P$^{30}$]hGH-RH(1-29)NH$_2$ |
| P-11703 | [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, Har$^{20}$, Orn$^{21}$, Nle$^{27}$, D-Arg$^{28}$, Har$^{29}$-AE$_4$P$^{30}$]hGH-RH(1-29)NH$_2$ |
| P-11704 | [(CH$_3$—(CH$_2$)$_{10}$-CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_4$P$^{30}$]hGH-RH(1-29)NH$_2$ |

Especially preferred are peptides having the formula shown in Table B below:

TABLE B

| | |
|---|---|
| P-1109 | [PhAc$^0$-Tyr$^1$, D-Arg$^2$, Cpa$^6$, Ala$^8$, Har$^9$, Tyr(Me)$^{10}$, His$^{11}$, Abu$^{15}$, Glu$^{17}$, His$^{20}$, Nle$^{27}$, D-Arg$^{28}$, Har$^{29}$]hGH-RH(1-29)NH$_2$ |
| P-11109 | [Dca$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11111 | [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11113 | [Fer$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11115 | [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11117 | [(PhAc-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11119 | [(Ac-Ada-D-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11123 | [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11125 | [(CH$_3$—(CH$_2$)$_{10}$-CO-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11209 | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Apa$^{30}$]hGH-RH(1-29)NH$_2$ |
| P-11213 | [Oct$^0$-Tyr$^1$, D-Arg$^2$, Cpa$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11307 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Amc$^{30}$]hGH-RH(1-29)NH$_2$ |
| P-11313 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Agm$^{30}$]hGH-RH(1-29) |
| P-11317 | [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$ |
| P-11408 | [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11433 | [Nac$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$ |
| P-11435 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11457 | [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11459 | [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11469 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11473 | [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11479 | [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11485 | [(CH$_3$—(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11491 | [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11497 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11499 | [PhAc$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11521 | [(Dca-Amc)$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11601 | [(CH$_3$—(CH$_2$)$_{10}$-CO-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11602 | [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11604 | [(PhAc-Ada)$^0$-Tyr$^1$, D-Arg$^2$, (Phe(F)$_5$)$^6$, Ala$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-29)NH$_2$ |
| P-11606 | [(PhAc-Ada)$^1$-Tyr', D-Arg$^2$, (Phe(F)$_5$)$^6$, (Me-Ala)$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-29)NH$_2$ |
| P-11610 | [PhAc$^0$-Tyr$^1$, D-Arg$^2$, Cpa$^6$, Ala$^8$, Har$^9$, (Phe(F)$_5$)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11612 | [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |

Most preferred are peptides having the formula shown in Table C below:

TABLE C

| | |
|---|---|
| P-11109 | [Dca$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11113 | [Fer$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11117 | [(PhAc-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11119 | [(Ac-Ada-D-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11123 | [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11125 | [(CH$_3$—(CH$_2$)$_{10}$-CO-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11213 | [Oct$^0$-Tyr$^1$, D-Arg$^2$, Cpa$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11307 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Amc$^{30}$]hGH-RH(1-29)NH$_2$ |
| P-11313 | [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Agm$^{30}$]hGH-RH(1-29)NH$_2$ |
| P-11317 | [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$ |
| P-11408 | [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$ |
| P-11433 | [Nac$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$ |
| P-11435 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11457 | [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11459 | [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11469 | [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11473 | [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11485 | [(CH$_3$—(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |
| P-11491 | [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11601 | [(CH$_3$—(CH$_2$)$_{10}$-CO-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11602 | [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ |
| P-11604 | [(PhAc-Ada)$^0$-Tyr$^1$, D-Arg$^2$, (Phe(F)$_5$)$^6$, Ala$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-29)NH$_2$ |
| P-11606 | [(PhAc-Ada)$^0$-Tyr', D-Arg$^2$, (Phe(F)$_5$)$^6$, (Me-Ala)$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-29)NH$_2$ |
| P-11610 | [PhAc$^0$-Tyr$^1$, D-Arg$^2$, Cpa$^6$, Ala$^8$, Har$^9$, (Phe(F)$_5$)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$ |

C. Method of Preparation

Overview of Synthesis

The peptides are synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, Ill., 1984 (2nd. ed.), and M. Bodanszky, "Principles of Peptide Synthesis", Springer Verlag, 1984. The hGH-RH antagonist peptides are preferably prepared using solid phase synthesis, such as that generally described by Merrifield, J. Am. Chem. Soc., 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group. In certain cases, protected omega-amino acids are also used during the synthesis. Boc and Fmoc protecting groups are also appropriate for the protection of omega-amino groups.

In solid phase synthesis, the N-alpha-protected or N-omega-protected amino acid moiety which forms the aminoacyl group of the final peptide at the C-terminus is attached to a polymeric resin support via a chemical link. After completion of the coupling reaction, the alpha (or omega) amino protecting group is selectively removed to allow subsequent coupling reactions to take place at the amino-terminus, preferably with 50% TFA in DCM when the N-alpha-(N-omega-) protecting group is Boc, or by 20% piperidine in DMF when the N-alpha-(N-omega-) protecting group is Fmoc. The remaining amino acids with similarly Boc or Fmoc-protected alpha (or omega) amino groups are coupled stepwise to the free amino group of the preceding amino acid on the resin to obtain the desired peptide sequence. Because the amino acid residues are coupled to the alpha (or omega) amino group of the C-terminus residue, growth of the synthetic hGH-RH analogue peptides begins at the C terminus and progresses toward the N-terminus. When the desired sequence has been obtained, the peptide is acylated at the N-terminus, and it is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha (or omega) amino protecting group prior to the coupling of the next amino acid.

Typical synthesis cycles are shown in Table I and Table II.

TABLE I

Protocol for a Typical Synthetic Cycle Using Boc-strategy

| Step | Reagent | Mixing Time (min) |
|---|---|---|
| 1. Deprotection | 50% TFA in DCM | 5 + 25 |
|  | DCM wash | 1 |
|  | 2-propanol wash | 1 |
| 2. Neutralization | 5% DIEA in DCM | 1 |
|  | DCM wash | 1 |
|  | MeOH wash | 1 |
|  | 5% DIEA in DCM | 3 |
|  | MeOH wash | 1 |
|  | DCM wash (3 times) | 1 |
| 3. Coupling | 3 eq. Boc-amino acid in DCM or DMF + 3 eq. DIC or the preformed HOBt ester of the Boc-amino acid | 60 |
|  | MeOH wash (3 times) | 1 |
|  | DCM wash (3 times) | 1 |
| 4. Acetylation (if appropriate) | $Ac_2O$ in pyridine (30%) | 10 + 20 |
|  | MeOH wash (3 times) | 1 |
|  | DCM wash (3 times) | 1 |

TABLE II

Protocol for a Typical Synthetic Cycle Using Fmoc-strategy

| Step | Reagent | Mixing Time (min) |
|---|---|---|
| 1. Deprotection | 20% piperidine in DMF | 5 + 15 |
|  | DMF wash (3 times) | 1 |
| 2. Coupling | 3 eq. Fmoc-amino acid in DMF + 3 eq. DIC or +3 eq. HBTU + 3 eq. HOBt + 6 eq. DIEA DMF wash (3 times) | 60 |
|  |  | 1 |
| 3. Acetylation (if appropriate) | 3 eq. 1-acetylimidazole in DMF | 30 |
|  | DMF wash (3 times) | 1 |

After completion of the synthesis, the cleavage of the peptide from the resin can be effected using procedures well known in peptide chemistry.

2. Choice of the Support Polymer.

The hGH-RH antagonist peptides may be synthesized on a variety of support polymers, i.e. MBHA, Merrifield, PAM, Rink amide or Wang resins. The peptides can also be synthesized on aminomethyl, MBHA, or other resins that have been previously derivatized with suitable linkers. Examples of such linkers are the base-labile 4-hydroxymethyl benzoic acid (HMBA) linker for the attachment of C-terminal carboxyl groups or the acid-labile para-sulfonyl-phenoxyacetyl (SPA) linker which permits the attachment of agmatine through its guanidino group.

When peptides with an amidated C-terminus are synthesized by using Boc strategy, the preferred resin is MBHA. Attachment of the C-terminal amino acid to this resin can be accomplished by the standard DIC-mediated coupling method described in Table I.

In order to prepare peptides with a C-terminal ethylamide (—NHEt) modification, the Merrifield resin or HMBA-MBHA resin can be used in conjunction with the Boc strategy. Loading of the C-terminal amino acid onto the Merrifield resin is done by coupling mediated by potassium fluoride (KF) or cesium salt at elevated temperature.

For the synthesis of peptides having Agm at the C-terminus, it is preferred that the support phase is MBHA resin or an aminomethyl resin. The guanidino group of Boc-Agm is joined to the support polymer through a stable, but readily cleavable linker such as the para-sulfonyl-phenoxyacetyl (SPA) moiety. The alpha-amino-Boc-protected Agm is reacted with the chlorosulfonyl phenoxyacetic acid Cl-SO$_2$—C$_6$H$_4$—O—CH$_2$—COOH to form Boc-Agm-SO$_2$—C$_6$H$_4$—O—CH$_2$—COOH. This compound is then coupled to the support polymer e.g. to MBHA resin using DIC or HBTU-HOBt-DIEA as activating reagent to yield Boc-Agm-SPA-MBHA.

3. Amino Acid Derivatives Used.

Bifunctional amino acids, i.e. those not having side chain functional groups, are mostly used in the form of their N-alpha Boc- or Fmoc-derivatives for synthesis. Bifunctional omega-amino acids are also typically used in the form of their N-omega Boc- or Fmoc-derivatives. Thus, Boc-Gly-OH or Fmoc-Gly-OH is typically used for incorporating the Gly residue. The naturally occurring bifunctional amino acids are Gly, Ala, Val, Leu, Ile, Phe, and Pro, and some well-known non-coded bifunctional amino acids used in this invention are Abu, Aib, and Nle.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the reactions used to form the peptides. The following general rules are followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

When Boc-amino acids are used in the synthesis, the reactive side chain functional groups can be protected as follows: Tos or nitro (NO$_2$) for Arg and Har; cHx or Fm for Asp and Glu; Bom for His; 2ClZ or Fmoc for Lys and Orn; Bzl for Ser and Thr; For Trp; and 2BrZ for Tyr. The side chains of Asn and Gln are unprotected. In the case of Fmoc synthesis, the reactive side chain functional groups can be protected by other appropriate protective groups as follows: 2,2,4,6,7-pentamethyl-dihydrobenzofurane-5-sulfonyl (Pbf) or bis-Boc for Arg and Har; tert-butyl (tBu) for Asp and Glu; no protective group or trityl (Trt) protection for Asn and Gln; Trt for His; Boc or 4-methoxytrityl (Mmt) for Lys and Orn; tBu or Trt for Ser and Thr; Boc for Trp; and tBu or 2-chlorotrityl (2ClTrt) for Tyr.

In addition to the widely known coded and non-coded amino acids mentioned above, some of the peptides of this application contain less common non-coded amino acids such as homoarginine (Har); ornithine (Orn); O-methyl-tyrosine [Tyr(Me)]; pentafluoro-phenylalanine [Phe(F)$_5$]; para-amidino-phenylalanine (Amp); para-guanidino-phenylalanine (Gup); cyclohexylalanine (Cha); 1,2,3,4-tetrahydronorharman-3-carboxylic acid (Tpi); (2-naphthyl) alanine (2-Nal); (3,3-diphenyl)alanine (Dip); para-amino-phenylalanine [Phe(pNH$_2$)]; para-nitro-phenylalanine [Phe(pNO$_2$)]; (3-pyridyl)alanine (3-Pal); O-ethyl-tyrosine [Tyr (Et)]; and para-benzoyl-phenylalanine (Bpa). These amino acid residues are incorporated into the peptides by coupling the suitable protected amino acid derivatives. A non-exclusive list of such protected amino acid derivatives that can be used is as follows: Boc-Amp(Alloc)-OH, Boc-Amp-OH, Fmoc-Amp(Alloc)-OH, Fmoc-Amp-OH, Boc-Gup(Tos)-OH, Boc-Gup-OH, Fmoc-Gup(Boc)$_2$-0H, Fmoc-Gup-OH, Boc-Cha-OH, Boc-Tpi-OH, Boc-2-Nal-OH, Boc-Dip-OH, Boc-Phe(pNH—Z)—OH, Boc-Phe(pNO$_2$)-0H, Boc-3-Pal-OH, Boc-Tyr(Et)-OH, Boc-Tyr(Me)-OH, Boc-Phe(F)$_5$-0H, and Boc-Bpa-OH. The protected derivatives of noncoded amino acids mentioned above are commonly available from several commercial suppliers, including Bachem (King of Prussia, Pa.), Peptides International (Louisville, Ky.), Novabiochem (San Diego, Calif.), Advanced ChemTech (Louisville, Ky.), and RSP Amino Acid Analogues DBA (Worcester, Mass.), and AnaSpec (San Jose, Calif.).

4. Stepwise Coupling of Amino Acid Residues

Utilizing the above mentioned support polymers and after loading of the C-terminal amino acid or Agm residue, the peptide itself may suitably be built up by solid phase synthesis in the conventional manner. Each protected amino acid is coupled in about a three-fold molar excess, with respect to resin-bound free amino residues, and the coupling may be carried out in a medium such as DMF-DCM (1:1) or in DMF or DCM alone. The selection of an appropriate coupling reagent is within the skill of the art. Particularly suitable as coupling reagents are N,N'-diisopropyl carbodiimide (DIC), or HBTU combined with HOBt in the presence of DIEA. The success of the coupling reaction at each stage of the synthesis is preferably monitored by the ninhydrin reaction. In cases where incomplete coupling occurs, either the coupling procedure is repeated, or the resin-bound unreacted amino residues are acetylated using a capping reagent, before removal of the alpha (or omega) amino protecting group. Suitable capping reagents are 1-acetylimidazole and Ac$_2$O-pyridine.

Final acylation of the N-terminus of the peptide with monocarboxylic acids is done in the same way as the previous couplings, with the difference that the appropriate carboxylic acid is used instead of an amino acid. When dicarboxylic acids are attached to the N-terminus and it is desired that only one —COOH group reacts with the amino terminus of the peptide (that is, monoamides of these acids are prepared), the anhydrides of the respective dicarboxylic acids can be used for coupling. The cyclic anhydrides of many dicarboxylic acids are commercially available; in other cases the preformed anhydrides of these acids are prepared by treatment with DIC and used for coupling.

5. Cleavage of the Peptide from the Support Polymer and Removal of the Side-Chain Protecting Groups When the synthesis is complete, the peptide is cleaved from the support phase and its side-chain protecting groups are removed.

In cases where peptides with an amidated C-terminus (—CONH$_2$) or with a C-terminal carboxyl group (—COOH) are prepared by Boc strategy on an MBHA, Merrifield, or PAM resin, the removal of the peptide from the resin is performed by treatment with a reagent such as liquid hydrogen fluoride (HF). This is also the case for peptides synthesized on the Boc-Agm-SPA-MBHA resin. In some instances, the liquid HF also cleaves all the remaining side chain protecting groups. However, if side chain protecting groups resistant to HF treatment are present on the peptide, additional cleavage steps should be performed in order to remove these protecting groups. Thus, Fm and Fmoc protecting groups are removed by treatment with 20% piperidine in DMF, while All and Alloc groups are removed by treatment with Pd(PPh$_3$)$_4$ catalyst and nucleophilic scavengers, prior to or after the HF treatment.

Suitably, the dried and protected peptide-resin is treated with a mixture consisting of 1.0 ml m-cresol and 10 ml anhydrous hydrogen fluoride per gram of peptide-resin for 60-120 min at O°—C. to cleave the peptide from the resin as well as to remove the HF-130abile side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

In cases where peptides with an ethylamide (—NHEt) C-terminus are prepared by Boc strategy on the Merrifield or HMBA-MBHA resin, the protected peptides are first cleaved from the resin by ethylamine (EtNH$_2$) mediated aminolysis. Suitably, liquid EtNH$_2$ is transferred into a cooled, heavy-walled glass flask that contains the dried and protected peptide-resin. The quantity of liquid EtNH$_2$ should be sufficient to cover the peptide-resin. The flask is stoppered, and shaken with the liquid EtNH$_2$ for 3.5 hours at room temperature in order to allow for the reaction to take place. After this, the flask is cooled in a dry ice bath, opened, and the liquid EtNH$_2$ is filtered off the solid residue that contains a mixture of resin and cleaved peptide, the peptide still having the protecting groups attached. The solid residue is dried and subjected to HF treatment as described above, in order to remove the side chain protecting groups of the peptide.

6. Purification.

The purification of the crude peptides can be effected using procedures well known in peptide chemistry. For example, purification may be performed on a MacRabbit HPLC system (Rainin Instrument Co. Inc., Woburn, Mass.) with a Knauer UV Photometer and a Kipp and Zonen BD40 Recorder using a Vydac 218TP51 0 reversed-phase column (10×250 mm, packed with C18 silica gel, 300 Å pore size, 5 u.m particle size) (The Separations Group Inc., Hesperia, Calif.). The column is eluted with a solvent system consisting of (A) 0.1% aqueous TFA and (B) 0.1% TFA in 70% aqueous MeCN in a linear gradient mode (e.g., 30-55% B in 120 min). The eluent is monitored at 220 nm, and fractions are examined by analytical HPLC using a Hewlett-Packard Model HP-1090 liquid chromatograph and pooled to give maximum purity. Analytical HPLC is carried out on a Vydac 218TP52 reversed-phase column (2×250 mm, C18, 300 Å, 5 µm) using isocratic elution with a solvent system consisting of (A) and (B) defined above. The peaks are monitored at 220 and 280 nm. The peptides are judged to be substantially (>95%) pure by analytical HPLC. Molecular masses are checked by electrospray mass spectrometry, and the expected amino acid compositions are confirmed by amino acid analysis.

D. Pharmaceutical Compositions and Mode of Administration.

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred antagonists are salts of low solubility, e.g., pamoate salts and the like. These exhibit long duration of activity.

The compounds of the present invention are suitably administered to subject humans or animals subcutaneously (s.c.), intramuscularly (i.m.), or intravenously (i.v); intranasally or by pulmonary inhalation; by transdermal delivery; or in a depot form (e.g., microcapsules, microgranules, or cylindrical rod like implants) formulated from a biodegradable suitable polymer (such as D,L-lactide-coglycolide), the former two depot modes being preferred. Other equivalent modes of administration are also within the scope of this invention, i.e., continuous drip, cutaneous patches, depot injections, infusion pump and time release modes such as microcapsules and the like. Administration is in any physiologically acceptable injectable carrier, physiological saline being acceptable, though other carriers known to the art may also be used.

The peptides are preferably administered parenterally, intramuscularly, subcutaneously or intravenously with a pharmaceutically acceptable carrier such as isotonic saline. Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed antagonistic compounds.

The amount of peptide needed depends on the type of pharmaceutical composition and on the mode of administration. In cases where human subjects receive solutions of GH-RH antagonists, administered by i.m. or s.c. injection, or in the form of intranasal spray or pulmonary inhalation, the typical doses are between 2-20 mg/day/patient, given once a day or divided into 2-4 administrations/day. When the GH-RH antagonists are administered intravenously to human patients, typical doses are in the range of 8-80 μg/kg of body weight/day, divided into 1-4 bolus injections/day or given as a continuous infusion. When depot preparations of the GH-RH antagonists are used, e.g. by i.m. injection of pamoate salts or other salts of low solubility, or by i.m. or s.c. administration of microcapsules, microgranules, or implants containing the antagonistic compounds dispersed in a biodegradable polymer, the typical doses are between 1-10 mg antagonist/day/patient.

E. Therapeutic Uses of GH-RH Antagonists

The most important therapeutic applications of GH-RH antagonists are expected to be in the field of oncology and endocrinology. Some of the GH-RH antagonists act predominantly at the pituitary level and have stronger endocrine effects, inhibiting the GH-RH-evoked GH release, and ultimately decreasing the serum levels of GH and IGF-1. Other GH-RH antagonists act predominantly at the tumor level, by blocking the tumoral receptors for GH-RH, reducing the production of various autocrine/paracrine tumor growth factors (such as IGF-1, IGF-11, GH, VEGF, FGF) and/or downregulating their receptors (IGF-1 receptors, GH receptors, VEGF receptors, FGF receptors, EGF receptors EGFR, human epidermal growth factor receptors HER2, HER3, and HER4), in addition to inhibiting the intracellular signaling pathways involved in the proliferation and survival of the cancer cells, and thus exert stronger inhibitory effects on tumor growth. These antagonists can also be used as carrier systems linked to radionuclides for tumor localization or therapy, or conjugated to chemotherapeutic agents or toxins. Such hybrid compounds can be actively targeted to cancer for diagnostic or therapeutic purposes. Yet other GH-RH antagonists act by multiple mechanisms of action, that is by endocrine mechanisms and by direct effects on tumors at the same time. Thus, the main therapeutic indications of various GH-RH antagonists differ based on their preferential mechanism of action.

Analogs of GH-RH with antagonistic action on the pituitary can be used in situations where it is beneficial to suppress serum levels of GH and IGF1I. Thus they are indicated for the therapy of endocrine disorders characterized by excessive production of GH and IGF-1, as well as for the treatment of cancers that express receptors for IGF-1, IGF-11, or GH, and the proliferation of which is stimulated by these growth factors.

Somatostatin analogs and GH antagonists are also available for the treatment of endocrine conditions caused by GH and IGF-1. However, GH-RH antagonists offer unique therapeutical benefits unobtainable by the use of somatostatin analogs and GH antagonists.

These benefits are due to the multiple mechanisms of action of GH-RH antagonists, namely that they exert GH- and IGF-1-independent direct effects on tumors and other target sites, in addition to inhibiting the endocrine axis for GH and IGF-1. GH-RH antagonists may be given alone or together with somatostatin analogs, a combination which more completely suppresses GH and IGF-1 levels. An undesired side-effect of GH antagonists, which can be avoided by the administration of GH-RH antagonists, is the elevation of serum GH levels through a feed-back mechanism.

One disease caused by excess growth hormone is acromegaly, which is manifested in an abnormal enlargement of the bones of the face and extremities. GH-RH antagonists could alleviate the clinical manifestations of acromegaly, e.g. the enlargement of facial and extremity bones, the enlargement of heart, and other structural and functional abnormalities of the cardiovascular system. The GH-RH antagonists may also be used to treat diabetic retinopathy (the main cause of blindness in diabetics) and diabetic nephropathy, in which damage to the eye and kidney respectively is thought to be due to GH. Diabetic patients can also benefit from the increased insulin sensitivity produced by GH-RH antagonists, an effect linked to the ability of these compounds to reduce the GH and IGF-1 levels. In addition, since they inhibit GH release, GH-RH antagonists can be used to slow down the progression of muscular dystrophy.

Drugs with anti-growth factor properties such as GH-RH antagonists can also be of benefit in controlling or slowing down the progression of some clinicopathologic processes in conditions such as idiopathic pulmonary fibrosis, systemic sclerosis and hypertrophic cardiomyopathy, where the present medical therapies have relatively little to offer. In addition, no drug therapy has been shown to be effective in decreasing the incidence of restenosis after percutaneous transluminal coronary angioplasty (PTCA) and new approaches must be devised, including the use of GH-RH antagonists. Some gynecologic conditions, such as myoma, endometriosis, and polycystic ovary syndrome, can also be treated with GH-RH antagonists in combination with luteinizing hormone-releasing hormone (LH-RH) agonists or antagonists. GH-RH antagonists are also available for treatment of benign prostatic hyperplasia (BPH), and hyperplastic and benign proliferative disorders of other normal organs in which the GH-RH receptors are present. In addition, GH-RH antagonists can be of benefit for the treatment of autoimmune diseases including multiple sclerosis.

However, the main applications of GH-RH antagonists are in the field of cancer. GH-RH antagonists, especially those with strong direct effects at the tumor level, are indicated for the inhibition of growth of primary tumors and for the suppression of their metastatic spread. Since the antiproliferative effects of GH-RH antagonists are exerted by several mechanisms, these compounds are available for the treatment of a large variety of cancers, such as those that depend on autocrine/paracrine and endocrine stimulation by GH-RH, IGF-1, IGF-11, GH, VEGF, and FGF, and cancers dependent on growth factor receptors such as GH-RH receptors, IGF-1 receptors, GH receptors, VEGF receptors, FGF receptors, and receptors of the EGF receptor/HER family (EGF receptors or HER1, HER2, HER3, and HER4). GH-RH antagonists also inhibit the phosphorylation of MAP kinases $ERK_{1/2}$, c-jun kinase JNK, and the phosphorylation of AKT, and thus are available for the treatment of cancers dependent on the MEK-ERK and PI3K-AKT-mTOR signaling pathways. In addition, GH-RH antagonists decrease the levels of cyclo-oxygenase 2 (COX2), and mutant Ras proteins. Thus, GH-RH antagonists are also available for the treatment of cancers dependent on the mentioned proliferative and anti-apoptotic (survival) signaling pathways, signaling molecules, and oncoproteins. For maximum therapeutic benefits, GH-RH antagonists are available for use as single therapeutic agents, or in combination therapeutic regimens with chemotherapeutic and cytotoxic agents, targeted therapeutic agents, and radiotherapy.

GH-RH antagonists are available for the treatment of tumors that express GH-RH receptors and use GH-RH as an autocrine/paracrine growth factor. Such malignancies include, but are not limited to, cancers of the lung, prostate, breast, ovary, endometrium, esophagus, stomach, intestine, pancreas, kidney, urinary bladder, bone, liver, as well as glioblastomas, pheochromocytomas, melanomas, and lymphomas. By blocking the tumoral receptors for GH-RH, these antagonists prevent the stimulatory action of GH-RH, resulting in inhibition of tumor growth.

One advantage of GH-RH antagonists over somatostatin analogs is based on the fact that GH-RH antagonists may be utilized for suppression of tumors which do not have somatostatin receptors but express the tumoral receptors for GH-RH, for example human osteogenic sarcomas.

Malignancies that express the IGF-1 receptors, and depend on IGF-1 and/or IGF-11 as growth factors, are available for therapy with GH-RH antagonists. These malignancies include, among others, lung cancers, prostatic, breast, ovarian, endometrial, gastric, colorectal, pancreatic, renal, and hepatic cancers, sarcomas, and brain tumors. The ability of GH-RH antagonists to decrease serum IGF-I levels, inhibit the autocrine/paracrine production of IGF-1 and/or IGF-11 in the tumor tissue, and downregulate the expression level of IGF-1 receptor, is beneficial for cancer therapy.

Breast cancers and other types of cancer that depend on GH as a growth factor, can be treated with GH-RH antagonists. The ability of GH-RH antagonists to reduce serum GH levels, inhibit the autocrine production of GH, and downregulate GH receptor expression, beneficiate the treatment of certain breast cancers and other types of tumors as well.

GH-RH antagonists are available as inhibitors of angiogenesis, in view of their inhibitory activity on the synthesis of VEGF, bFGF, and their receptors (receptors for VEGF and bFGF) by tumor tissues and normal endothelial cells, and considering their antiproliferative effect on endothelial cells. Thus GH-RH antagonists could be beneficial for the treatment of those tumors that strongly depend on VEGF, bFGF, and neoangiogenesis.

EXAMPLES

The present invention is described in connection with the following examples which are set forth for the purposes of illustration only. In the examples, optically active protected amino acids in the L-configuration are used except where specifically noted.

The following Examples set forth suitable methods of synthesizing the novel GH-RH antagonists by the solid-phase technique.

Example I $(CH_3(CH_2)_{10}CO-Ada)^0-Tyr^1-D-Arg^2-Asp^3-Ala^4-Ile^5-Cpa^6-Thr^7-Ala^8-Har^9-Tyr(Me)^{10}-His^{11}-Lys^{12}-Var^3-Leu^{14}-Abui^{15}-Gln^{16}-Leu^{17}-Ser^{18}-Ala^{19}-His^{20}-Lys^{21}-Leu^{22}-Leu^{23}-Gln^{24}-Asp^{25}-Ile^{26}-Nle^{27}-D-Arg^{28}-Har^{29}-NH_2$ (Peptide 11125)

$[(CH_3(CH_2)_{10}CO-Ada)^0-Tyr^1, D-Arg^2, Cpa^6, Ala^8, Har^9, Tyr(Me)^{10}, His^{11}, Abu^{15}, His^{20}, Nle^{27}, D-Arg^{28}, Har^{29}]hGH-RH(1-29)NH_2$

The synthesis is conducted in a stepwise manner using manual solid phase peptide synthesis equipment. Briefly, para-methylbenzhydrylamine (MBHA) resin (Bachem, King of Prussia, Pa.) (720 mg, 0.50 mmol) is neutralized with 5% DIEA in DCM and washed according to the protocol described in Table I. The solution of Boc-Har($NO_2$)—OH (500 mg, 1.5 mmol) in DMF-DCM (1:1) is shaken with the neutralized resin and DIC (235 µl, 1.5 mmol) in a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har($NO_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH.

These protected amino acid residues (also commonly available from Bachem, Novabiochem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µl, 1.5 mmol) with the exceptions of Boc-Asn-OH and Boc-Gln-OH which are coupled with their preformed HOBt esters. After removal of the $N^{(omega)}$-Boc protecting group from Ada°, the peptide is acylated overnight with dodecanoic acid $[CH_3(CH_2)_{10}COOH]$ (601 mg, 3 mmol) using DIC (235 µl, 1.5 mmol) as a coupling agent.

In order to cleave the peptide from the resin and deprotect it, a portion of 250 mg of the dried peptide resin is stirred with 0.5 ml m-cresol and 5 ml hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 135 mg crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 135 mg of crude peptide is dissolved in AcOH/$H_2O$, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 15.5 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 1109, Peptide 1111, Peptide 11113, Peptide 11115, Peptide 11117, Peptide 11107, Peptide 11109, Peptide 11111, Peptide 11113, Peptide 11115, Peptide 11117, Peptide 11119, Peptide 11121, Peptide 11123, Peptide 11207, Peptide 11209, Peptide 11211, Peptide 11213, Peptide 11215, Peptide 11307, Peptide 11309, Peptide 11315, Peptide 11317, Peptide 11319, Peptide 11321, Peptide 11407, Peptide 11408, Peptide 11409, Peptide 11411, Peptide 11413, Peptide 11417, Peptide 11419, Peptide 11421, Peptide 11423, Peptide 11425, Peptide 11427, Peptide 11429, Peptide 11431, Peptide 11433, Peptide 11435, Peptide 11437, Peptide 11439, Peptide 11441, Peptide 11443, Peptide 11445, Peptide 11447, Peptide 11449, Peptide 11451, Peptide 11453, Peptide 11455, Peptide 11457, Peptide 11459, Peptide 11461, Peptide 11463, Peptide 11465, Peptide 11467, Peptide 11469, Peptide 11471, Peptide 11473, Peptide 11475, Peptide 11477, Peptide 11479, Peptide 11481, Peptide 11483, Peptide 11485, Peptide 11487, Peptide 11491, Peptide 11497, Peptide 11499, Peptide 11501, Peptide 11503, Peptide 11513, Peptide 11515, Peptide 11521, Peptide, Peptide 11525, Peptide 11601, Peptide 11602, Peptide 11603, Peptide 11610, Peptide, Peptide 11612, Peptide 11620, Peptide 11621, Peptide 11630, Peptide 11701, Peptide 11702, Peptide 11703, and Peptide 11704 are synthesized in the same manner as Peptide 11125, except that these peptides also contain other amino acid substitutions in the peptide sequence, different C-termini, and other acyl moieties at their N-termini. The details for these syntheses are set forth below.

For the synthesis of Peptide 1109, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, Glu$^{17}$, His$^{20}$, D-Arg$^{28}$, Har$^{29}$]hGH-RH(1-29) $NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Lys(2ClZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har($NO_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 1111, the chemical structure of which is [PhAc$^0$-Tyr$^1$, D-Arg$^2$, (Me-Ala)$^4$, Cpa$^6$, Ala$^8$, Har$^9$, Tyr(Me)$^{10}$, His$^{20}$, Abu$^{15}$, His$^{20}$, Nle$^{27}$, D-Arg$^{28}$, Har29]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har($NO_2$)—OH, Boc-Ala-OH, Boc-Thr(Bzl)-OH, Boc-Cpa-OH, Boc-Ile-OH, Boc-(Me-Ala)-OH, Boc-Asp(OcHx)-OH, Boc-D-Arg(Tos)-OH, Boc-Tyr(2BrZ)-OH, followed by acylation with PhAc—OH.

For the synthesis of Peptide 1113, the chemical structure of which is [PhAc$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)$NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har($NO_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 1115, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$] hgH-RH (1-29) $NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(Me)$_2$-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har($NO_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH. For the synthesis of Peptide 1117, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hgH-RH (1-29) $NH_2$, the following protected amino acids are coupled in the indicated order on the MBHA resin: Boc-Har($NO_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(Me)$_2$-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Me)$_2$-OH, Boc-His(Bom)-OH, Boc-Tyr(Me)-OH, Boc-Har($NO_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11107, the chemical structure of which is [(N-Me-Aib)$^0$-Tyr$^1$ D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)$NH_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, and Boc-(N-Me-Aib)-OH. For the synthesis of Peptide 11109, the chemical structure of which is [Dca$^0$-Tyr$^1$ D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-—OH, Boc-Leu-OH, Boc-Gln-OH, Boc-Abu-OH, Boc-Leu-OH, Boc-Val-OH, Boc-Lys(2ClZ)—OH, Boc-His(Bom)-OH, Boc-Tyr(Me)-OH, Boc-Har(NO$_2$)—OH, Boc-Ala-OH, Boc-Thr(Bzl)-—OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-OH.

For the synthesis of Peptide 11111, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH. For the synthesis of Peptide 11113, the chemical structure of which is [Fer$^0$-Tyr$^1$, D-Arg$^2$, Cpa$^6$, Ala$^8$, Har$^9$, Tyr(Me)$^{10}$, His$^{11}$, Abu$^{15}$, His$^{20}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)—OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Fer-OH.

For the synthesis of Peptide 11115, the chemical structure of which is [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11117, the chemical structure of which is [(PhAc-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with PhAc—OH.

For the synthesis of Peptide 11119, the chemical structure of which is [(Ac-Ada-D-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-D-Phe-OH, Boc-Ada-OH, followed by acylation with Ac—OH. For the synthesis of Peptide 11121, the chemical structure of which is [(Ac-Ada-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Phe-OH, Boc-Ada-OH, followed by acylation with Ac—OH. For the synthesis of Peptide 11123, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11207, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc- His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11209, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Apa$^{30}$] hGH-RH(1-29)NH$_2$, the following protected amino acids are coupled in the indicated order on the MBHA resin: Boc-Apa-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11211, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$] hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11213, the chemical structure of which is [Oct$^0$-Tyr$^1$, D-Arg$^2$, Cpa$^6$, Ala$^8$, Har$^9$, Tyr(et)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)-OH, Boc-His(Bom)-OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Oct-OH.

For the synthesis of Peptide 11215, the chemical structure of which is [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$] hGH-RH(1-29)NH$_2$, the following protected amino acids are coupled in the indicated order on the MBHA resin: Boc-Ada-OH, Boc-Arg(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11307, the chemical structure of which is [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11309, the chemical structure of which is [(Me-NH-Sub)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Me-NH-Sub-OH.

For the synthesis of Peptide 11315, the chemical structure of which is [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$] hGH-RH(1-29)NH$_2$ the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11317, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$] hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11319, the chemical structure of which is [(Ac-Ada)$^0$-Tyr$^1$, D-Arg$^2$, Cpa$^6$, Ala$^8$, Har$^9$, Tyr(et)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc- Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Et)-OH, Boc-His(Bom)-OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11321, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$] hGH-RH(1-29)NH$_2$, the following protected amino acids are coupled in the indicated order on the MBHA resin: Boc-Ada-OH, Boc-Arg(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11407, the chemical structure of which is [(Ac-Amc)$^0$-Tyr$^1$, D-Arg$^2$, (Me-Ala$^4$)Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$] hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-(Me-Ala)-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11408, the chemical structure of which is [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har29] hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11409, the chemical structure of which is [(Ac-Amc)$^0$-Tyr$^1$, D-Arg$^2$, (Me-Ala)$^4$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-(Me-Ala)-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11411, the chemical structure of which is [PhAc$^0$-Tyr$^1$, D-Arg$^2$, (Me-Ala)$^4$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11413, the chemical structure of which is [PhAc$^0$-Tyr$^1$, D-Arg$^2$, Cpa$^6$, 3-Pal$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$] hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-3-Pal-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11417, the chemical structure of which is [(Ac-Amc)$^0$-Tyr$^1$, D-Arg$^2$, (Me-Ala)$^4$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11419, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11421, the chemical structure of which is [(N-Me-Aib)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Leu-OH, Boc-Gln-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, and Boc-(N-Me-Aib)-OH.

For the synthesis of Peptide 11423, the chemical structure of which is [PhAc$^0$-Tyr$^1$, D-Arg$^2$, Cpa$^6$, Dip$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Dip-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11321, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$]hGH-RH(1-29)NH$_2$, the following protected amino acids are coupled in the indicated order on the MBHA resin: Boc-Ada-OH, Boc-Arg(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11407, the chemical structure of which is [(Ac-Amc)$^0$-Tyr$^1$, D-Arg$^2$, (Me-Ala)$^4$, Cpa$^6$, Ala$^8$, Har$^9$, Tyr(Me)$^{10}$, His$^{11}$, Abu$^{15}$, His$^{20}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-(Me-Ala)-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11408, the chemical structure of which is [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11409, the chemical structure of which is [(Ac-Amc)$^0$-Tyr$^1$, D-Arg$^2$, (Me-Ala)$^4$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-(Me-Ala)-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11411, the chemical structure of which is [PhAc$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11413, the chemical structure of which is [PhAc$^0$-Tyr$^1$, D-Arg$^2$, Cpa$^6$, 3-Pal$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-3-Pal-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11417, the chemical structure of which is [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11419, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11421, the chemical structure of which is [(N-Me-Aib)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, and Boc-(N-Me-Aib)-OH.

For the synthesis of Peptide 11423, the chemical structure of which is [PhAc$^0$-Tyr$^1$, D-Arg$^2$, Cpa$^6$, Dip$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Dip-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11425, the chemical structure of which is [PhAc$^0$-Tyr$^1$, D-Arg$^2$, Cpa$^6$, Ala$^8$, Har$^9$, Tyr(Me)$^{10}$, His$^{11}$, Lys(PhAc-Tyr-D-Arg-Asp-Ala-Ile-Cpa-Thr-Ala-Har-Tyr(Me)-His)$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Boc)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.F or the synthesis of Peptide 11427, the chemical structure of which is [(N-Me-Aib)$^0$-Tyr$^1$, D-Arg$^2$, Cpa$^6$, Ala$^8$, Har$^9$, Tyr(Me)$^{10}$, His$^{11}$, Lys((N-Me-Aib)-Tyr-D-Arg-Asp-Ala-Ile-Cpa-Thr-Ala-Har-Tyr(Me)-His)$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Boc)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, and Boc-(N-Me-Aib)-OH.

For the synthesis of Peptide 11429, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$, the MBHA resin is first loaded with Boc-Lys(Fmoc)-OH, followed by removal of the Fmoc protecting group as described in Table II (section 1. Deprotection), and acylation of the ε-amino group of Lys with octanoic acid (Oct-OH). Subsequently, the rest of the peptide chain is constructed in the usual way, using Boc strategy, by coupling the following protected amino acids in the indicated order: Boc-β-Ala-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11431, the chemical structure of which is [(N-Me-Aib)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D Arg$^{28}$, Har$^{29}$-β-Ala$^{30}$-Lys(Oct)$^{31}$]hGH-RH(1-29)NH$_2$, the MBHA resin is first loaded with Boc-Lys(Fmoc)-OH, followed by removal of the Fmoc protecting group as described in Table II (section 1. Deprotection), and acylation of the ε-amino group of Lys with octanoic acid (Oct-OH). Subsequently, the rest of the peptide chain is constructed in the usual way, using Boc strategy, by coupling the following protected amino acids in the indicated order: Boc-β-Ala-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, and Boc-(N-Me-Aib)-OH.

For the synthesis of Peptide 11433, the chemical structure of which is [Nac$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Nac-OH.

For the synthesis of Peptide 11435, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin:

Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11437, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11439, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(Me)$_2$-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11441, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, (Lys(Me)$_2$)$^{12}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(Me)$_2$-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Me)$_2$-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11443, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(Me)$_2$-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11445, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, (Lys(Me)$_2$)$^{12}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(Me)$_2$-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Me)$_2$-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11447, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Har$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Har(NO$_2$)—OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11449, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Har$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-Har(NO$_2$)—OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11451, the chemical structure of which is [(Nac-Ada)$^0$-Tyr$^1$\D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Nac-OH.

For the synthesis of Peptide 11453, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca—OH.

For the synthesis of Peptide 11455, the chemical structure of which is [(Ac-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, the following protected amino acids are coupled in the indicated order on the MBHA resin: Boc-AE$_2$A-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)-OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11457, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11459, the chemical structure of which is [(PhAc-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with PhAc—OH.

For the synthesis of Peptide 11461, the chemical structure of which is [(Ac-Ada-Phe)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Phe-OH, Boc-Ada-OH, followed by acylation with Ac—OH.

For the synthesis of Peptide 11463, the chemical structure of which is [PhAc$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AMC$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11465, the chemical structure of which is [PhAc$^0$-Tyr$^1$ D-Arg$^2$, Cpa$^6$, Ala$^8$, Har$^9$, Tyr(Me)$^{10}$, His$^{11}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11467, the chemical structure of which is [Ada-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, and Boc-Ada-OH.

For the synthesis of Peptide 11469, the chemical structure of which is [Ac-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11471, the chemical structure of which is [(Ac-Ada)$^0$-Tyr$^1$ D-Arg$^2$, Cpa$^6$, Ala$^8$, Har$^9$, Tyr (Me)[10], His[11], Lys(Ac-Ada-Tyr-D-Arg-Asp-Ala-Ile-Cpa-Thr-Ala-Har-Tyr(Me)-His-)[12], Abu[15], His[20], Orn[21], Nle[27], D-Arg[28], Har[29]]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Boc)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11473, the chemical structure of which is [(PHAc-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with PhAc—OH.

For the synthesis of Peptide 11475, the chemical structure of which is [(Ac-Ada-D-Phe)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-D-Phe-OH, Boc-Ada-OH, followed by acylation with Ac—OH.

For the synthesis of Peptide 11477, the chemical structure of which is [(Ac-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)—OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11479, the chemical structure of which is [(Ac-Ada)$^0$-Tyr$^1$ D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11481, the chemical structure of which is [(Ac-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-ε-Lys(α-NH$_2$)$^{30}$-Ahx$^{31}$]hGH-RH(1-29)NH$_2$, the following protected amino acids are coupled in the indicated order on the MBHA resin: Boc-Ahx-OH, Z-Lys(Boc)-OH, Boc-Har(NO$_2$)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11483, the chemical structure of which is [(Ac-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_4$P$^{30}$]hGH-RH(1-29)NH$_2$, the following protected amino acids are coupled in the indicated order on the MBHA resin: Boc-AE$_4$P—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11485, the chemical structure of which is [(CH$_3$(CH$_2$)$_{10}$CO-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with CH$_3$(CH$_2$)$_{10}$COOH.

For the synthesis of Peptide 11487, the chemical structure of which is [(CH$_3$(CH$_2$)$_{10}$CO-Ada)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc- Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with CH$_3$(CH$_2$)$_{10}$COOH.

For the synthesis of Peptide 11491, the chemical structure of which is [(Dca-Ada)$^0$-Tyr$^1$ D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$—OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11497, the chemical structure of which is [(Ac-Amc)$^0$-Tyr$^1$ D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$ Ada$^{30}$]hGH-RH(1-29)NH$_2$, the following protected amino acids are coupled in the indicated order on the MBHA resin: Boc-Ada-OH, Boc-Har(NO$_2$)O, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11499, the chemical structure of which is [PhAc$^0$-Tyr$^1$ D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$ Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$—OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11501, the chemical structure of which is [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$, the MBHA resin is first loaded with Boc-Lys(Fmoc)-OH, followed by removal of the Fmoc protecting group as described in Table II (section 1. Deprotection), and acylation of the ε-amino group of Lys with octanoic acid (Oct-OH). Subsequently, the rest of the peptide chain is constructed in the usual way, using Boc strategy, by coupling the following protected amino acids in the indicated order: Boc-β-Ala-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11503, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$, the MBHA resin is first loaded with Boc-Lys(Fmoc)-OH, followed by removal of the Fmoc protecting group as described in Table II (section 1. Deprotection), and acylation of the ε-amino group of Lys with octanoic acid (Oct-OH). Subsequently, the rest of the peptide chain is constructed in the usual way, using Boc strategy, by coupling the following protected amino acids in the indicated order: Boc-β-Ala-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11513, the chemical structure of which [(Dca$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$] hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Har(NO$_2$)—OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Dca-OH.

For the synthesis of Peptide 11515, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Lys(Dca-Ada-Tyr-D-Arg-Asp-Ala-Ile-Cpa-Thr-Ala-Har-Tyr(Me-His')$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(Boc)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11521, the chemical structure of which is [(Dca-Amc)$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Orn(2CIZ)-OH, Boc-Leu-OH, Boc-Val-OH, Boc-Orn(2CIZ)-

OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Dca-OH.

For the synthesis of Peptide 11523, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, Glu$^{17}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-Orn(2CIZ)-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11525, the chemical structure of which is [PhAc$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Orn(2CIZ)-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11601, the chemical structure of which is [(CH$_3$(CH$_2$)$_{10}$CO-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)-OH, Boc-Ala-OH, Boc-Thr(Bzl)-OH, Boc-Phe(F)$_5$—OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with CH$_3$(CH$_2$)$_{10}$COOH.

For the synthesis of Peptide 11602, the chemical structure of which is [(CPhAc-Ada)-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$-0H, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with PhAc—OH.

For the synthesis of Peptide 11603, the chemical structure of which is [(DCA-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2CIZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$-0H, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11610, the chemical structure of which [PhAc$^0$-Tyr$^1$, D-Arg$^2$, Cpa$^6$, Ala$^8$, Har$^9$, (Phe(F)$_5$)$^6$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Phe(F)$_5$—OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with PhAc—OH.

For the synthesis of Peptide 11611, the chemical structure of which is [(Ac-Amc)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$—OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11612, the chemical structure of which is [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Phe(F)$_5$-0H, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11620, the chemical structure of which [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$] hGH-RH(1-29)NH$_2$, the following protected amino acids are coupled in the indicated order on the MBHA resin: Boc-Ada- OH, Boc-Arg(Tos)-OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys (2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with Ac—OH.

For the synthesis of Peptide 11621, the chemical structure of which is [(Me-NH-Sub$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Ada-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2CIZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, followed by acylation with Me-NH-Sub-OH.

For the synthesis of Peptide 11630, the chemical structure of which is [(Ac-Ada)$^0$-Tyr$^1$, D-Arg$^2$, Cpa$^6$, (Me-ala)$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$, the following protected amino acids are coupled in the indicated order on the MBHA resin: Boc-Amc-OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2CIZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Ac—OH.

For the synthesis of Peptide 11701, the chemical structure of which is [(Dca-Ada)$^0$-Tyr$^1$, D-Arg$^2$, Cpa$^6$, Ala$^8$, Har$^9$, Tyr(Me)$^{10}$, His$^1$, Orn$^{12}$, Abu$^{15}$, Glu$^{17}$, Orn$^{21}$, Nle$^{27}$, D-Arg$^{28}$, Har$^{29}$-AE$_4$P$^{30}$]hGH-RH(1-29)NH$_2$, the following protected amino acids are coupled in the indicated order on the MBHA resin: Boc-AE$_4$P—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Arg(Tos)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11702, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, His$^{20}$, Orn$^2$, Nle$^{27}$, D-Arg$^{28}$, Har$^{29}$-AE$_4$P$^{30}$]hGH-RH(1-29)NH$_2$, the following protected amino acids are coupled in the indicated order on the MBHA resin: Boc-AE$_4$P—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11703, the chemical structure of which is [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, Har$^{20}$, Orn$^{21}$, Nle$^{27}$, D-Arg$^{28}$, Har$^{29}$-AE$_4$P$^{30}$]hGH-RH(1-29)NH$_2$, the following protected amino acids are coupled in the indicated order on the MBHA resin: Boc-AE$_4$P—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-Har(NO2)-OH, Boc-Ala-OH, Boc-Ser(Bzl)-OH, Boc-Glu(OcHx)-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with Dca-OH.

For the synthesis of Peptide 11704, the chemical structure of which is [(CH$_3$(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_4$P$^{30}$]hGH-RH(1-29)NH$_2$, the following protected amino acids are coupled in the indicated order on the MBHA resin: Boc-AE$_4$P—OH, Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2CIZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH, followed by acylation with CH$_3$(CH$_2$)$_{10}$COOH.

HF cleavage and deprotection, and subsequent purification by semipreparative HPLC of Peptide 1109, Peptide 1111, Peptide 1113, Peptide 1115, Peptide 1117, Peptide 11107, Peptide 11109, Peptide 11111, Peptide 11113, Peptide 11115, Peptide, Peptide 11119, Peptide 11121, Peptide 11123, Peptide 11207, Peptide 11209, Peptide, Peptide 11213, Peptide 11215, Peptide 11307, Peptide 11309, Peptide 11315, Peptide 11317, Peptide 11319, Peptide 11321, Peptide 11407, Peptide 11408, Peptide 11409, Peptide 11411, Peptide 11413, Peptide 11417, Peptide 11419, Peptide 11421, Peptide 11423, Peptide 11425, Peptide 11427, Peptide 11429, Peptide 11431, Peptide 11433, Peptide 11435, Peptide 11437, Peptide 11439, Peptide 11441, Peptide 11443, Peptide 11445, Peptide 11447, Peptide 11449, Peptide 11451, Peptide 11453, Peptide 11455, Peptide 11457, Peptide 11459, Peptide 11461, Peptide 11463, Peptide 11465, Peptide 11467, Peptide 11469, Peptide 11471, Peptide 11473, Peptide 11475, Peptide 11477, Peptide 11479, Peptide 11481, Peptide 11483, Peptide 11485, Peptide 11487, Peptide 11491, Peptide 11497, Peptide 11499, Peptide 11501, Peptide 11503, Peptide 11513, Peptide 11515, Peptide 11521, Peptide 11523, Peptide 11525, Peptide 11601, Peptide 11602, Peptide 11603, Peptide 11610, Peptide 11611, Peptide 11612, Peptide 11620, Peptide 11621, Peptide 11630, Peptide 11701, Peptide 11702, Peptide 11703, and Peptide 11704 are done as described in the case of Peptide 11125. The purified compounds are judged to be substantially (>95%) pure by analytical HPLC. Their molecular masses are checked by electrospray mass spectrometry, and the expected amino acid compositions are confirmed by amino acid analysis.

Example II (Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Agm$^{30}$] hGH-RH(1-29) (Peptide 11313). The synthesis is conducted in a stepwise manner using manual solid phase peptide synthesis equipment. The starting material of the synthesis is Boc-agmatine-N$^G$-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin has been described in U.S. Pat. No. 4,914,189 and in the scientific literature (Zarandi M, Serfozo P, Zsigo J, Bokser L, Janaky T, Olsen D B, Bajusz S, Schally A V, Int. J. Peptide Protein Res. 39: 211-217, 1992), hereby incorporated by reference. Briefly, Boc-Agm-SPA-MBHA resin (1.67 g, 0.50 mmol) is pre-swollen in DCM and then the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)—OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH. The protected amino acids (1.5 mmol each) are coupled with DIC (235 µl, 1.5 mmol) with the exceptions of Boc-Asn-OH and Boc-Gln-OH which are coupled with their preformed HOBt esters. After removal of the N$^\omega$-Boc protecting group from Amc$^0$, the peptide is acylated with 1-acetylimidazole (220 mg, 2 mmol).

In order to cleave the peptide from the resin and deprotect it, a portion of 500 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 210 mg of crude product is obtained.

The peptide is purified by semipreparative H PLC and the eluting fractions are examined by analytical HPLC as described in Example I. Fractions with purity higher than 95% are pooled and lyophilized to give 33.0 mg of pure Peptide 11313. Molecular mass is checked by electrospray mass spectrometry, and the expected amino acid composition is confirmed by amino acid analysis.

Peptide 11311, and Peptide 11415 are synthesized in the same manner as Peptide 11313, except that these peptides also contain other substitutions.

For the synthesis of Peptide 11311, the chemical structure of which is [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, D-Arg$^{28}$, Agm$^{29}$]hGH-RH(1-29), the following protected amino acids are coupled in the indicated order on the Boc-Agm-SPA-MBHA resin: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(Me)-OH, Boc-Har(NO$_2$)—OH, Boc-Ala-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with 1-acetylimidazole.

For the synthesis of Peptide 11415, the chemical structure of which is [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Agm$^{30}$]hGH-RH(1-29), the following protected amino acids are coupled in the indicated order on the Boc-Agm-SPA-MBHA resin: Boc-Har(NO$_2$)—OH, Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Lys(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Lys(2ClZ)-OH, Boc-His(Bom)-OH, Boc-Tyr(Me)-OH, Boc-Har(NO$_2$)—OH, Boc-(Me-Ala)-OH, Boc-Thr(Bzl)-OH, Boc-Cpa-OH, Boc-Ile-OH, Boc-Ala-OH, Boc-Asp(OcHx)-OH, Boc-D-Arg(Tos)-OH, Boc-Tyr(2BrZ)-OH, Boc-Amc-OH, followed by acylation with 1-acetylimidazole.

HF cleavage and deprotection, and subsequent purification by semipreparative HPLC of Peptide 11311 and Peptide 11415 are done as described in the case of Peptide 11313. The purified compounds are judged to be substantially (>95%) pure by analytical HPLC. Their molecular masses are checked by electrospray mass spectrometry, and the expected amino acid compositions are confirmed by amino acid analysis.

Example III (PhAc-Ada)$^0$-Tyr$^1$-D-Arg$^2$-Asp$^3$-Ala$^4$-Ile$^5$-(Phe(F)$_5$)$^6$-Thr$^7$-Ala$^8$-Har$^9$-Tyr(Me)$^{10}$-His$^{11}$-Orn$^{12}$-Val$^{13}$-Leu$^{14}$-Abu$^{15}$-Gln$^{16}$-Leu$^{17}$-Ser$^{18}$-Ala$^{19}$-His$^{20}$-Orn$^{21}$-Leu$^{22}$-Leu$^{23}$-Gln$^{24}$-Asp$^{25}$-Ile$^{26}$-Nle$^{27}$-D-Arg$^{28}$-Har$^{29}$-Agm$^{30}$. (Peptide 11604) [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-30)

The synthesis is conducted in a stepwise manner using manual solid phase peptide synthesis equipment. The starting material of the synthesis is Boc-agmatine-N$^G$-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin has been described in U.S. Pat. No. 4,914,189 and in the scientific literature (Zarandi M, Serfozo P, Zsigo J, Bokser L, Janaky T, Olsen D B, Bajusz S, Schally A V, Int. J. Peptide Protein Res. 39: 211-217, 1992), hereby incorporated by reference. Briefly, Boc-Agm-SPA-MBHA resin (1.67 g, 0.50 mmol) is pre-swollen in DCM and then the deprotection and neutralization protocols described in Table I are performed in order to remove the Boc protecting group and prepare the peptide-resin for coupling of the next amino acid. The solution of Boc-Har(NO$_2$)—OH (500 mg, 1.5 mmol) in DMF-DCM (1:1) is shaken with the neutralized resin and DIC (235 µL, 1.5 mmol) in a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn (2CIZ)-OH, Boc-His(Bom)-OH, Boc-Tyr(Me)-OH, Boc-Har($NO_2$)—OH, Boc-Ala-OH, Boc-Thr(Bzl)-OH, Boc-Phe($F)_5$-OH, Boc-Ile-OH, Boc-Ala-OH, Boc-Asp(OcHx)-OH, Boc-D-Arg(Tos)-OH, Boc-Tyr(2BrZ)-OH, Boc-Ada-OH.

These protected amino acid residues (also commonly available from Bachem) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters. After removal of the $N^{omega}$-Boc protecting group from $Ada^0$, the peptide is acylated with phenylacetic acid (PhAc—OH) (272 mg, 2 mmol) using DIC (313 μL, 2 mmol) as a coupling agent.

In order to cleave the peptide from the resin and deprotect it, a portion of 500 mg of the dried peptide resin is stirred with 0.5 ml m-cresol and 5 ml hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 220 mg of crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 220 mg of crude peptide is dissolved in $AcOH/H_2O$, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 10 mL/min. The eluent is monitored at 220 nm, and fractions are examined by analytical HPLC. Fractions with purity higher than 95% are pooled and lyophilized to give 35.0 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

Example IV (PhAc-Ada)$^0$-Tyr$^1$-D-Arg$^2$-Asp$^3$-Ala$^4$-Ile$^5$-(Phe$(F)_5)^6$-Thr$^7$-(Me-Ala)$^8$-Har$^9$-Tyr(Me)$^{10}$-His$^{11}$-Orn$^{12}$-Val$^{13}$-Leu$^{14}$-Abu$^{15}$-Gln$^{16}$-Leu$^{17}$-Ser$^{18}$-Ala$^{19}$-His$^{20}$-Orn$^{21}$-Leu$^{22}$-Leu$^{23}$-Gln$^{24}$-Asp$^{25}$-Ile$^{26}$-Nle$^{27}$-D-Arg$^{28}$-Har$^{29}$-Agm$^{30}$. (Peptide 11606) [(PhAc-Ada)$^0$-Tyr$^1$, D-Arg$^2$, (Phe$(F)_5)^6$, (Me-Ala)$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-30)

The synthesis is conducted in a stepwise manner using manual solid phase peptide synthesis equipment. The starting material of the synthesis is Boc-agmatine-$N^G$-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin has been described in U.S. Pat. No. 4,914,189 and in the scientific literature (Zarandi M, Serfozo P, Zsigo J, Bokser L, Janaky T, Olsen D B, Bajusz S, Schally A V, Int. J. Peptide Protein Res. 39: 211-217, 1992), hereby incorporated by reference. Briefly, Boc-Agm-SPA-MBHA resin (1.67 g, 0.50 mmol) is pre-swollen in DCM and then the deprotection and neutralization protocols described in Table I are performed in order to remove the Boc protecting group and prepare the peptide-resin for coupling of the next amino acid. The solution of Boc-Har($NO_2$)—OH (500 mg, 1.5 mmol) in DMF-DCM (1:1) is shaken with the neutralized resin and DIC (235 μL, 1.5 mmol) in a manual solid phase peptide synthesis apparatus for 1 hour. After the completion of the coupling reaction is proved by negative ninhydrin test, the deprotection and neutralization protocols described in Table I are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-D-Arg(Tos)-OH, Boc-Nle-OH, Boc-Ile-OH, Boc-Asp(OcHx)-OH, Boc-Gln-OH, Boc-Leu-OH, Boc-Leu-OH, Boc-Orn(2CIZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn (2CIZ)-OH, Boc-His(Bom)-OH, Boc-Tyr(Me)-OH, Boc-Har($NO_2$)—OH, Boc-(Me-Ala)-OH, Boc-Thr(Bzl)-OH, Boc-Phe$(F)_5$—OH, Boc-Ile-OH, Boc-Ala-OH, Boc-Asp(OcHx)-OH, Boc-D-Arg(Tos)-OH, Boc-Tyr(2BrZ)-OH, Boc-Ada-OH.

These protected amino acid residues (also commonly available from Bachem) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 μL, 1.5 mmol) with the exceptions of Boc-Asn-OH and Boc-Gln-OH which are coupled with their preformed HOBt esters. After removal of the $Nomes^a$-Boc protecting group from $Ada^0$, the peptide is acylated with phenylacetic acid (PhAc—OH) (272 mg, 2 mmol) using DIC (313 μL, 2 mmol) as a coupling agent.

In order to cleave the peptide from the resin and deprotect it, a portion of 500 mg of the dried peptide resin is stirred with 0.5 ml m-cresol and 5 ml hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 216 mg of crude product is obtained.

The crude peptide is checked by analytical HPLC using a Hewlett-Packard Model HP-1090 liquid chromatograph with a Supelco Discovery HS C18 reversed-phase column (2.1 mm×5 cm, packed with C18 silica gel, 120 Å pore size, 3 μm particle size) (Supelco, Bellefonte, Pa.) and linear gradient elution (e.g., 40-70% B), with a solvent system consisting of (A) 0.1% aqueous TFA and (B) 0.1% TFA in 70% aqueous MeCN. For purification by semipreparative HPLC, 216 mg of crude peptide is dissolved in $AcOH/H_2O$, stirred, filtered and applied on a Beckman Ultraprep ODS column (21.2 mm×15 cm, packed with C18 silica gel, 300 Å pore size, 10 μm particle size). The column is eluted with a solvent system described above in a linear gradient mode (e.g., 40-60% B in 120 min); flow rate 10 mL/min. The eluent is monitored at 220 nm, and fractions are examined by analytical HPLC. Fractions with purity higher than 95% are pooled and lyophilized to give 33.0 mg pure product. The analytical HPLC is carried out on a Supelco C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

Example V

Aqueous Solution for Intramuscular Injection

| | |
|---|---|
| [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$ (Peptide 11602) | 500.0 mg |
| Gelatin, nonantigenic | 5.0 mg |
| Water for injection q.s. | ad 100.0 mL |

The gelatin and GH-RH antagonist Peptide 11602 are dissolved in water for injection, and then the solution is sterile filtered.

Example VI

Long Acting Intramuscular Injectable Formulation (Sesame Oil Gel)

| | |
|---|---|
| [(PhAc-Ada)$^0$-Tyr$^1$, D-Arg$^2$, (Phe(F)$_5$)$^6$, Ala$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-30) (Peptide 11604) | 10.0 mg |
| Aluminum monostearate, USP | 20.0 mg |
| Sesame oil q.s. | ad 1.0 mL |

The aluminum monostearate is combined with the sesame oil and heated to 125° C. with stiffing until a clear yellow solution forms. This mixture is then autoclaved for sterility and allowed to cool. The GH-RH antagonist Peptide 11604 is then added aseptically with trituration. Particularly preferred antagonists are salts of low solubility, e.g., pamoate salts and the like. These exhibit long duration of activity.

Example VII

Long Acting Intramuscular (IM) Injectable-Biodegradable Polymer Microcapsules Microcapsules are made from the following:

| | |
|---|---|
| 25/75 glycolide/lactide copolymer (0.5 intrinsic viscosity) | 99% |
| [(PhAc-Ada)$^0$-Tyr$^1$, D-Arg$^2$, (Phe(F)$_5$)$^6$, (Me-Ala)$^8$, Har$^9$, Tyr(Me)$^{10}$, His$^{12}$, Orn$^{12}$, Abu$^{15}$, His$^{20}$, Orn$^{21}$, Nle$^{27}$, D-Arg$^{28}$, Har$^{29}$, Agm$^{30}$]hGH-RH(1-30) (Peptide 11606) | 1% |

25 mg of the above microcapsules are suspended in 1.0 mL of the following vehicle:

| | |
|---|---|
| Dextrose | 5.0% |
| CMC, sodium | 0.5% |
| Benzyl alcohol | 0.9% |
| Tween 80 | 0.1% |
| Water, purified q.s. | ad 100% |

Biological Activity in Endocrine and Oncological Assays

The peptides of the present invention were tested in assays in vitro and in vivo for their ability to inhibit the hGH-RH(1-29)NH$_2$ induced GH release. Binding affinities of the compounds to the tumoral GH-RH receptors were also measured. The antitumor activities of the peptides and their inhibitory effects on serum IGF-1 and on the tumoral IGF, VEGF and FGF system were evaluated in various cancer models in vivo. Inhibitory effects on phosphorylated PI3K/AKT and MAPK (ERK1/2) were also measured.

Example VIII

Effect of GH-RH Antagonists on PC-3 Human Prostate Cancer Xenografts in Nude Mice

Experiment 1

Male nude mice were implanted s.c. with 3 mm$^3$ pieces of PC-3 human hormone-independent prostate cancer tissue on both flanks. When tumors reached a volume of approx. 50 mm$^3$, the mice were divided into 4 experimental groups with 8 to 10 animals in each group and received single daily injections for 35 days as follows: 1. Control (vehicle solution); 2. JMR-132 (10 µg/day s.c.); 3.Peptide 1109 (10 µg/day s.c.); 4.Peptide 11111 (10 µg/day s.c.); Tumor volumes were measured once a week. The experiment was ended on day 35 by sacrificing the mice under Isoflurane anesthesia. Resulting tumors were cleaned, weighed, and snap-frozen until further analyses. Statistical analyses of the measurement results were done by two-tailed t-test, p<0.05 being considered significant. Data are presented as the means±S.E.

Experiment 2

Experiment 2 was similar to Experiment 1. Experiment 2 was started when PC-3 tumors had grown to approximately 50 mm$^3$ in volume. At this time, the animals were divided into 5 experimental groups with 8 animals in each group, and received single daily injections for 14 days as follows: 1. Control (vehicle solution); 2. JMR-132 (10 µg/day s.c.); 3.Peptide 1109 (5 µg/day s.c.); 4.Peptide 11109 (5 µg/day s.c.); 5.Peptide 11109 (2 µg/day s.c.). Further details of Experiment 2 are the same as for Experiment 1

Experiment 3

Male nude mice were implanted s.c. with 3 mm$^3$ pieces of PC-3 human hormone-independent prostate cancer tissue on both flanks. When tumors reached a volume of approximately 50 mm$^3$, the mice were divided into 12 experimental groups with 8 to 10 animals in each group and received single daily injections for 28 days as follows: 1. Control (vehicle solution); 2. JMR-132 (10 µg/day s.c.); 3.Peptide 11113 (2 µg/day s.c.); 4.Peptide 11119 (2 µg/day s.c.); 5.Peptide 11209 (2 µg/day s.c.); 6.Peptide 11313 (2 µg/day s.c.); 7.Peptide 11408 (2 µg/day s.c.); 8.Peptide 11435 (2 µg/day s.c.); 9.Peptide 11457 (2 µg/day s.c.); 10.Peptide 11459 (2 µg/day s.c.); 11.Peptide 11469 (2 µg/day s.c.); 12.Peptide 11491 (2 µg/day s.c.).

Tumor volumes were measured once a week. The experiment was ended on day 28 by sacrificing the mice under Isoflurane anesthesia. Resulting tumors were cleaned, weighed, and snap-frozen until further analyses. Statistical analyses of the measurement results were done by two-tailed t-test, p<0.05 being considered significant.

Experiment 4

All experimental details of Experiment 4 are the same as for Experiment 3, with the following difference. When tumors reached a volume of approximately 50 mm³, the mice were divided into 11 experimental groups with 8 to 10 animals in each group and received single daily injections for 46 days as follows: 1. Control (vehicle solution); 2. JMR-132 (10 µg/day s.c.); 3.Peptide 11123 (2 µg/day s.c.); 4.Peptide 11125 (2 µg/day s.c.); 5.Peptide 11213 (2 µg/day s.c.); 6.Peptide 11433 (2 µg/day s.c.); 7.Peptide 11473 (2 µg/day s.c.); 8.Peptide 11485 (2 µg/day s.c.); 9.Peptide 11497 (2 µg/day s.c.); 10.Peptide 11499 (2 µg/day s.c.); 11.Peptide 11521 (2 µg/day s.c.). Tumor volumes were measured once a week. The experiment was ended on day 46 by sacrificing the mice under Isoflurane anesthesia. Resulting tumors were cleaned, weighed, and snap-frozen until further analyses. Statistical analyses of the measurement results were done by two-tailed t-test, p<0.05 being considered significant.

Results

Experiment 1

Among the GH-RH antagonists tested, Peptide 1109 and Peptide 11111 exerted a significant inhibitory effect on the growth of PC-3 tumors, while the effect of reference peptide JMR-132 was not significant (Table III). Abreviated reference JMR-132 means [PhAc⁰-Tyr¹, D-Arg², Cpa⁶, Ala⁸, Har⁹, Tyr(Me)¹⁰, His¹¹, Abu₁₅, His²⁰, Nle²⁷, D-Arg²⁸, Har²⁹] hGH-RH(1-29)NH₂,

TABLE III

Experiment 1: Effect of Treatment with GH-RH Antagonists on PC-3 Human Prostate Cancer Xenografts in Nude Mice

| Group | Tumor growth after 5 weeks (%) | Significance versus control | Significance versus JMR-132 |
|---|---|---|---|
| Control | 6701 ± 2541 | | |
| JMR-132 | 2820 ± 498 | 0.15 (N.S.) | |
| Peptide 1109 | 1502 ± 405 | 0.048 | 0.0163 |
| Peptide 11111 | 1215 ± 243 | 0.043 | 0.00707 |

N.S., not significant

Experiment 2

Peptide 1109, used at a dose of 5 u.g/day, as well as Peptide 11109, used at the doses of 5 u.g/day and 2 µg/day, inhibited the growth of PC-3 tumors more potently than reference peptide JMR-132. The inhibitory effect of Peptides 1109 and 11109 at the two dose levels was highly significant (p<0.01), while the effect of JMR-132 had a lower significance level (p<0.05) (Table IV).

TABLE IV

Experiment 2: Effect of Treatment with GH-RH Antagonists on PC-3 Human Prostate Cancer Xenografts in Nude Mice

| Group | Tumor growth after 2 weeks (%) | Inhibition (%) | Significance versus control |
|---|---|---|---|
| Control | 716 | | |
| JMR-132 (10 µg/day) | 432 | 39.61 | p < 0.05 |
| Peptide 1109 (5 µg/day) | 311 | 56.58 | p < 0.01 |
| Peptide 11109 (5 µg/day) | 217 | 69.68 | p < 0.01 |
| Peptide 11109 (2 µg/day) | 318 | 55.55 | p < 0.01 |

Experiment 3

All peptides of the present application, tested at the dose of 2 µg/day, more potently inhibited the growth of PC-3 tumors than the reference peptide JMR-132 at a 5-fold dose of 10 µg/day. The inhibitory effect of Peptide 11313, Peptide 11435, Peptide 11457, Peptide 11469, and Peptide 11491 were statistically significant (p<0.01 and p<0.001). The effect of reference peptide JMR-132 was not significant statistically. The results are shown in Table V.

TABLE V

Experiment 3: Effect of Treatment with GH-RH Antagonists on PC-3 Human Prostate Cancer Xenografts in Nude Mice

| Group | Tumor growth inhibition after 4 weeks (%) | Significance versus control |
|---|---|---|
| JMR-132 (10 µg/day) | 28.11 | N.S. |
| Peptide 11113 (2 µg/day) | 29.37 | N.S. |
| Peptide 11119 (2 µg/day) | 32.03 | N.S. |
| Peptide 11209 (2 µg/day) | 48.04 | N.S. |
| Peptide 11313 (2 µg/day) | 78.20 | p < 0.01 |
| Peptide 11408 (2 µg/day) | 63.61 | N.S. |
| Peptide 11435 (2 µg/day) | 75.11 | p < 0.01 |
| Peptide 11457 (2 µg/day) | 85.98 | p < 0.001 |
| Peptide 11459 (2 µg/day) | 53.60 | N.S. |
| Peptide 11469 (2 µg/day) | 78.07 | p < 0.01 |
| Peptide 11491 (2 µg/day) | 72.43 | p < 0.01 |

N.S., not significant

Experiment 4

After 28 days of treatment, all peptides of the present application, given at a dose of 2 µg/day, more potently inhibited the growth of PC-3 tumors than the reference peptide JMR-132, which was administered at a 5-fold higher dose of 10 µg/day. (Table VI). The inhibitory effects of Peptide 11125, Peptide 11213, and Peptide 11473 were significant after 28 days (Table VI).

TABLE VI

Experiment 4: Effect of GH-RH Antagonists on PC-3 Human Prostate Cancer Xenografts in Nude Mice After 28 Days of Treatment

| Group | Tumor growth after 28 days (%) | Inhibition (%) | Significance versus control |
|---|---|---|---|
| Control | 1368 | | |
| JMR-132 (10 µg/day) | 1004 | 26.62 | N.S. |
| Peptide 11123 (2 µg/day) | 786 | 42.57 | N.S. |
| Peptide 11125 (2 µg/day) | 424 | 68.97 | p < 0.01 |
| Peptide 11213 (2 µg/day) | 651 | 52.41 | p < 0.05 |
| Peptide 11433 (2 µg/day) | 956 | 30.15 | N.S. |
| Peptide 11473 (2 µg/day) | 442 | 67.68 | p < 0.01 |

TABLE VI-continued

Experiment 4: Effect of GH-RH Antagonists on PC-3 Human Prostate Cancer Xenografts in Nude Mice After 28 Days of Treatment

| Group | Tumor growth after 28 days (%) | Inhibition (%) | Significance versus control |
|---|---|---|---|
| Peptide 11485 (2 µg/day) | 794 | 41.96 | N.S. |
| Peptide 11497 (2 µg/day) | 872 | 36.25 | N.S. |
| Peptide 11499 (2 µg/day) | 782 | 42.86 | N.S. |
| Peptide 11521 (2 µg/day) | 877 | 35.86 | N.S. |

N.S., not significant

At the end of experiment, after 46 days of treatment, Peptide 11125, Peptide 11213, Peptide 11473, Peptide 11485, and Peptide 11497 had a more potent inhibitory effect than reference peptide JMR-132 at a 5-fold dose (Table VII). At the end of the experiment, the inhibitory effects of Peptide 11125, Peptide 11213, Peptide 11473, and Peptide 11485 were statistically significant. Reference peptide JMR-132 had no significant inhibitory effect at the end of experiment (Table VII).

TABLE VII

Experiment 4: Effect of GH-RH Antagonists on PC-3 Human Prostate Cancer Xenografts in Nude Mice After 46 Days of Treatment

| Group | Tumor growth after 46 days (%) | Inhibition (%) | Significance versus control |
|---|---|---|---|
| Control | 3330 | | |
| JMR-132 (10 µg/day) | 1848 | 44.52 | N.S. |
| Peptide 11123 (2 µg/day) | 1849 | 44.48 | N.S. |
| Peptide 11125 (2 µg/day) | 1009 | 69.69 | p < 0.05 |
| Peptide 11213 (2 µg/day) | 1144 | 65.65 | p < 0.05 |
| Peptide 11433 (2 µg/day) | 1890 | 43.23 | N.S. |
| Peptide 11473 (2 µg/day) | 1072 | 67.80 | p < 0.05 |
| Peptide 11485 (2 µg/day) | 1257 | 62.24 | p < 0.05 |
| Peptide 11497 (2 µg/day) | 1658 | 50.22 | N.S. |
| Peptide 11499 (2 µg/day) | 2178 | 34.59 | N.S. |
| Peptide 11521 (2 µg/day) | 2427 | 27.11 | N.S. |

N.S., not significant

Example IX

Effect of GH-RH Antagonists on H-460 Human Non-Small Cell Lung Cancer (Non-SCLC) Xenografts in Nude Mice

Experiment 1

Male nude mice were implanted s.c. with 3 mm$^3$ pieces of H-460 human non-SCLC tumor tissue on both flanks. When tumors had grown to a mean volume of approximately 90 mm$^3$, the mice were randomly assigned into 4 experimental groups with 10 animals in each group and received single daily injections for 28 days as follows: 1. Control (vehicle solution); 2. JMR-132 (10 µg/day s.c.); 3.Peptide 1109 (10 µg/day s.c.); 4.Peptide 11111 (10 µg/day s.c.). Tumor volumes were measured once a week. The experiment was ended on day 28 by sacrificing the mice under Isoflurane anesthesia. Resulting tumors were cleaned, weighed, and snap-frozen until further analyses. Statistical analyses of the measurement results were done by two-tailed t-test, p<0.05 being considered significant. Data are presented as the means±S.E.

Experiment 2

Male nude mice were implanted s.c. with 3 mm$^3$ pieces of H-460 human non-SCLC tumor tissue on both flanks. When tumors had grown to a mean volume of approximately 90 mm$^3$, the mice were randomly assigned into 12 experimental groups with 8 to 10 animals in each group and received single daily injections for 28 days as follows: 1. Control (vehicle solution); 2. JMR-132 (10 µg/day s.c.); 3. Peptide 11109 (5 µg/day s.c.); 4. Peptide 11113 (5 µg/day s.c.); 5. Peptide 11119 (5 µg/day s.c.); 6. Peptide 11209 (5 µg/day s.c.); 7. Peptide 11313 (5 µg/day s.c.); 8. Peptide 11408 (5 µg/day s.c.); 9. Peptide 11435 (5 µg/day s.c.); 10. Peptide 11459 (5 µg/day s.c.); 11.Peptide 11469 (5 µg/day s.c.); 12.Peptide 11491 (5 µg/day s.c.). Tumor volumes were measured once a week. The experiment was ended on day 28 by sacrificing the mice under Isoflurane anesthesia. Resulting tumors were cleaned, weighed, and snap-frozen until further analyses. Statistical analyses of the measurement results were done by two-tailed t-test, p<0.05 being considered significant. Data are presented as the means±S.E.

Experiment 3

Male nude mice were implanted s.c. with 3 mm$^3$ pieces of H-460 human non-SCLC tumor tissue on both flanks. When tumors had grown to a mean volume of approximately 90 mm$^3$, the mice were randomly assigned into 8 experimental groups with 8 to 10 animals in each group and received single daily injections for 28 days as follows: 1. Control (vehicle solution); 2. JMR-132 (10 µg/day s.c.); 3. Peptide 11123 (5 µg/day s.c.); 4. Peptide 11125 (5 µg/day s.c.); 5. Peptide 11307 (5 µg/day s.c.); 6. Peptide 11317 (5 µg/day s.c.); 7. Peptide 11473 (5 µg/day s.c.); 8. Peptide 11485 (5 µg/day s.c.). Tumor volumes were measured once a week. The experiment was ended on day 28 by sacrificing the mice under Isoflurane anesthesia. Resulting tumors were cleaned, weighed, and snap-frozen until further analyses. Statistical analyses of the measurement results were done by two-tailed t-test, p<0.05 being considered significant.

Results

Experiment 1

Among the GH-RH antagonists tested, Peptide 1109 and Peptide 11111 exerted a significant inhibitory effect (p<0.01 and p<0.05, respectively) on the growth of H-460 tumors, while the effect of reference peptide JMR-132 was not significant (Table VIII). The antitumor effect of Peptide 1109 was also significantly higher (p<0.05) than that of the reference peptide JMR-132 (Table VIII).

TABLE VIII

Experiment 1: Effect of Treatment with GH-RH Antagonists on H-460 Human non-SCLC Tumor Xenografts in Nude Mice

| Group | Tumor growth after 4 weeks (%) | Significance versus control | Significance versus JMR-132 |
|---|---|---|---|
| Control | 4434 ± 1099 | | |
| JMR-132 | 2404 ± 604 | 0.081 (N.S.) | |
| Peptide 1109 | 1042 ± 181 | 0.004 | 0.042 |
| Peptide 11111 | 2005 ± 541 | 0.035 | 0.824 |

N.S., not significant

Experiment 2

All new peptides tested, with the exception of Peptide 11109, inhibited the growth of H-460 lung cancers in vivo at a dose of 5 µg/day. The inhibitory effects of Peptide 11459 and Peptide 11491 were statistically significant (p<0.05). Peptide 11109 had no effect. Reference peptide JMR-132, even at a two-fold increased dose of 10 μg/day, had no inhibitory effect and in fact non-significantly stimulated the growth of H-460 tumors (Table IX).

TABLE IX

Experiment 2: Effect of Treatment with GH-RH Antagonists on H-460 Human non-SCLC Tumor Xenografts in Nude Mice

| Group | Tumor growth after 4 weeks (%) | Inhibition (%) | Significance versus control |
|---|---|---|---|
| Control | 7894 ± 2040 | | |
| JMR-132 (10 μg/day) | 11537 ± 8215 | (−46.14) stimul. | 0.4941 |
| Peptide 11109 (5 μg/day) | 7890 ± 4127 | 0.05 | 0.6672 |
| Peptide 11113 (5 μg/day) | 6790 ± 3340 | 13.98 | 0.8533 |
| Peptide 11119 (5 μg/day) | 5254 ± 1524 | 33.44 | 0.6131 |
| Peptide 11209 (5 μg/day) | 6377 ± 2477 | 19.21 | 0.9499 |
| Peptide 11313 (5 μg/day) | 3091 ± 1215 | 60.84 | 0.0906 |
| Peptide 11408 (5 μg/day) | 3998 ± 1113 | 49.35 | 0.2042 |
| Peptide 11435 (5 μg/day) | 4170 ± 2064 | 47.17 | 0.4136 |
| Peptide 11459 (5 μg/day) | 2418 ± 923 | 69.36 | 0.0297 |
| Peptide 11469 (5 μg/day) | 4810 ± 1977 | 39.06 | 0.5182 |
| Peptide 11491 (5 μg/day) | 1926 ± 473 | 75.60 | 0.0106 |

N.S., not significant

Experiment 3

Peptide 11123, Peptide 11125, Peptide 11307, Peptide 11317, and Peptide 11473, tested at the dose of 5 μg/day, more potently inhibited the growth of H-460 lung tumors than the reference peptide JMR-132 at a 2-fold higher dose of 10 μg/day. The inhibitory effect of Peptide 11473 reached statistical significance (p<0.05) already after the first week of treatment, and it remained significant throughout the experiment. The results are shown in Table X.

TABLE X

Experiment 3: Effect of Treatment with GH-RH Antagonists on H-460 Human non-SCLC Tumor Xenografts in Nude Mice

| Group | Tumor growth inhibition after 4 weeks (%) |
|---|---|
| JMR-132 (10 μg/day) | 15.37 |
| Peptide 11123 (5 μg/day) | 35.74 |
| Peptide 11125 (5 μg/day) | 33.03 |
| Peptide 11307 (5 μg/day) | 30.98 |
| Peptide 11317 (5 μg/day) | 41.00 |
| Peptide 11473 (5 μg/day) | 54.64 |
| Peptide 11485 (5 μg/day) | 9.04 |

Example X

Effect of GH-RH Antagonists on MDA-MB-231 Human Estrogen Independent Breast Cancer Xenografts in Nude Mice Female nude mice were xenografted s.c. with MDA-MB-231 tumor tissue from donor animals. When tumors had grown to a mean volume of approximately 50 mm$^3$, the mice were randomly assigned into 2 experimental groups with 10 animals in each group and received single daily injections for 28 days as follows: 1. Control (vehicle solution); 2.Peptide 1109 (5 μg/day s.c.). Tumor volumes were measured once a week. The experiment was ended on day 28 by sacrificing the mice under Isoflurane anesthesia. Resulting tumors were cleaned, weighed, and snap-frozen until further analyses. Statistical analyses of the measurement results were done by two-tailed t-test, p<0.05 being considered significant.

Results

Peptide 1109 at a dose of 5 μg/day inhibited the growth of MDA-MB-231 human breast cancers in nude mice by about 75%. The inhibitory effect became statistically significant (p<0.05) after 2 weeks of treatment and it remained significant (p<0.05) for the rest of the experiment.

Example XI

Effect of GH-RH Antagonists on NCI-N87 Human Gastric Cancer Xenografts in Nude Mice NCI-N87 cancers were transplanted s.c. into both flank areas of 30 female nude mice. The mice were randomly assigned into 4 experimental groups with 6 to 9 animals in each group and received single daily injections for 77 days as follows: 1. Control (vehicle solution); 2. JMR-132 (10 μg/day s.c.); 3. Peptide 1109 (10 μg/day s.c.); 4. Peptide 11479 (10 μg/day s.c.). Tumor volumes were measured once a week. The experiment was ended on day 77 by sacrificing the mice under Isoflurane anesthesia. Resulting tumors were cleaned, weighed, and snap-frozen until further analyses. Statistical analyses of the measurement results were done by two-tailed t-test, p<0.05 being considered significant. Data are presented as the means±S.E.

Results

Peptide 1109 and Peptide 11479 had significant inhibitory effect (p<0.05) on the growth of NCI-N87 cancers in nude mice. Moreover, 6 out of 11 tumors regressed in the group treated with Peptide 1109. Reference antagonist JMR-132 was not effective. The results are shown in Table XI.

TABLE XI

Effect of Treatment with GH-RH Antagonists on NCI-N87 Human Gastric Cancer Xenografts in Nude Mice

| Group | Tumor growth after 77 days (%) | Tumor weights (mg) | Tumor doubling time (days)† | Number of tumors per group | Number of regressing tumors |
|---|---|---|---|---|---|
| Control | 442 ± 119 | 446 ± 147 | 42.0 ± 5.9 | 12 | 1 |
| JMR-132 | 409 ± 78 | 407 ± 175 | 40.8 ± 5.9 | 15 | 2 |
| Peptide 1109 | 225 ± 59* | 170 ± 52 | 93.6 ± 30.7 | 11 | 6 |
| Peptide 11479 | 235 ± 48* | 144 ± 41 | 156.7 ± 55.7* | 14 | 1 |

*p < 0.05 vs. control.
†Tumor doubling time was calculated without the regressing tumors.

Example XII

Effect of GH-RH Antagonists on Panc-1 Human Cancer Xenografts in Nude Mice

Panc-1 cancers were transplanted s.c. into both flank areas of 60 female nude mice, and allowed to grow for 105 days before starting the treatment with GH-RH antagonists. The mice were randomly assigned into 3 experimental groups with 8 animals in each group and received single daily injections for 36 days as follows: 1. Control (vehicle solution); 2. JMR-132 (10 μg/day s.c.); 3. Peptide 11457 (10 μg/day s.c.). Tumor volumes were measured once a week. The experiment was ended on day 82 by sacrificing the mice under Isoflurane anesthesia. Resulting tumors were cleaned, weighed, and snap-frozen until further analyses. Statistical analyses of the measurement results were done by two-tailed t-test, $p<0.05$ being considered significant. Data are presented as the means±S.E.

Results

Peptide 11457 powerfully inhibited the growth of Panc-1 human pancreatic cancers in nude mice for at least 82 days although the treatment was stopped after 36 days. Reference peptide JMR-132 was less effective. The results are shown in Table XII.

TABLE XII

Effect of Treatment with GH-RH Antagonists on Panc-1 Human Pancreatic Cancer Xenografts in Nude Mice

| Group | Tumor growth from day 1 to day 82 (%) | Tumor volume on day 82 ($mm^3$) | Tumor weights (mg) |
|---|---|---|---|
| Control | 3190 ± 710 | 2040 ± 1357 | 606 ± 340 |
| JMR-132 | 1730 ± 350 | 511 ± 221* | 185 ± 105* |
| Peptide 11457 | 740 ± 1220* | 262 ± 103* | 76 ± 166* |

*$p < 0.05$ vs. control

Example XIII

Effect of GH-RH Antagonists on SK-Hep-1 Human Hepatocellular Cancer Xenografts in Nude Mice SK-Hep-1 cancers were transplanted s.c. into both flank areas of 66 female nude mice, and allowed to grow for 47 days before starting the treatment with GH-RH antagonists. The mice were randomly assigned into 4 experimental groups with 8 animals in each group and received single daily injections for 135 days as follows: 1. Control (vehicle solution); 2. JMR-132 (10 μg/day s.c.); 3. Peptide 1109 (5 μg/day s.c.); 4. Peptide 1109 (10 μg/day s.c.). Tumor volumes were measured once a week. The experiment was ended on day 135 by sacrificing the mice under Isoflurane anesthesia. Resulting tumors were cleaned, weighed, and snap-frozen until further analyses. Statistical analyses of the measurement results were done by two-tailed t-test, $p<0.05$ being considered significant. Data are presented as the means±S.E.

Results

Peptide 1109, even in a lower dose of 5 μg/day, more potently inhibited the growth of SK-Hep-1 hepatic cancers than the reference peptide JMR-132 at a dose of 10 μg/day. The inhibitory effect of JMR-132 was not significant, however the effect of Peptide 1109 at the 10 μg/day dose level was statistically significant. In addition, Peptide 1109 caused total regression of 5 tumors out of 13 at a dose of 5 μg/day, and as many as 7 out of 13 tumors regressed at the higher dose of 10 μg/day. By comparison, in the group treated with 10 μg/day of JMR-132, only 2 tumors regressed out of 12. One tumor out of 10 also regressed in the control group (spontaneous regression occasionally occurs in untreated SK-Hep-1 cancers). The results are summarized in Table XIII.

TABLE XIII

Effect of Treatment with GH-RH Antagonists on SK-Hep-1 Human Hepatocellular Cancer Xenografts in Nude Mice

| Group | Tumor volume ($mm^3$) on day 135 | Tumor weights† (mg) | Number of tumors per group | Tumors with total regression |
|---|---|---|---|---|
| Control | 730 ± 434 | 1388 ± 843 (5) | 10 | 1 |
| JMR-132 (10 μg/day) | 615 ± 372 | 1006 ± 569 (7) | 12 | 2 |
| Peptide 1109 (5 μg/day) | 271 ± 98 | 565 ± 115 (6) | 13 | 5 |
| Peptide 1109 (10 μg/day) | 200 ± 123* | 605 ± 281 (4) | 13 | 7 |

†The numbers in parentheses show the number of tumors removed at autopsy.
*$p = 0.030$ vs control.

Example XIV

PC3 Prostate Cancer Data—Including Data for P11604 and P11606

Male nude mice were implanted s.c. with 3 $mm^3$ pieces of PC-3 human hormone-independent prostate cancer tissue on both flanks. When tumors reached a volume of approximately 50 $mm^3$, the mice were divided into 8 experimental groups with 8 to 10 animals in each group and received single daily injections for 28 days as follows: 1. Control (vehicle solution); 2. P-11513 2 μg/day; 3. P-11602 2 μg/day; 4. P-11602 μg/day; 5. P-11604 2 μg/day; 6. P-11606 2 μg/day; 7. P-11610 2 μg/day; 8. P-11610 1 μg/day.

Tumor volumes were measured once a week. The experiment was ended on day 28 by sacrificing the mice under Isoflurane anesthesia. Resulting tumors were cleaned, weighed, and snap-frozen until further analyses. Statistical analyses of the measurement results were done by two-tailed t-test, $p<0.05$ being considered significant.

TABLE XIV

Effect of new GHRH antagonists on PC3 androgen-independent prostate cancer

| | 0 | 7 | 14 | 21 | 28 days |
|---|---|---|---|---|---|
| | | TUMOR GROWTH (%) | | | |
| CONTROL | 100 | 331.28 | 590.95 | 1290.10 | 1857.23 |
| P-11513 2 ug/day | 100 | 212.49 | 420.81 | 823.51 | 1420.09 |
| P-11602 2 ug/day | 100 | 197.77 | 270.61 | 449.82 | 641.31 |
| P-11602 1 ug/day | 100 | 249.81 | 295.25 | 467.74 | 740.06 |
| P-11604 2 ug/day | 100 | 159.84 | 199.57 | 316.88 | 383.97 |
| P-11606 2 ug/day | 100 | 145.65 | 307.66 | 521.69 | 709.50 |
| P-11610 2 ug/day | 100 | 132.24 | 289.25 | 466.31 | 631.89 |
| P-11610 1 ug/day | 100 | 195.49 | 302.30 | 549.94 | 740.17 |
| | | TUMOR INHIBITION (%) | | | |
| P-11513 2 ug/day | | 35.86 | 28.79 | 30.80 | 23.54 |
| P-11602 2 ug/day | | 40.30 | 54.21 | 62.20 | 65.47 |
| P-11602 1 ug/day | | 24.59 | 50.04 | 60.70 | 60.15 |
| P-11604 2 ug/day | | 51.75 | 66.23 | 73.37 | 79.33 |
| P-11606 2 ug/day | | 56.03 | 47.94 | 56.16 | 61.80 |
| P-11610 2 ug/day | | 60.08 | 51.05 | 60.82 | 65.98 |
| P-11610 1 ug/day | | 40.99 | 48.84 | 53.79 | 60.15 |

Example XV

Effects of New GHRH Antagonists on Human Non-Small Cell Lung Cancer Cell Line H460

The aim of this study was to find out the tumor inhibitor effect of the latest GHRH antagonists (Peptide 11423, Peptide 11602, Peptide 11604, Peptide 11606) on H460 human non-small cell lung cancer cell line. Female nude mice were xenografted subcutaneously with approximately 3 mm$^3$ pieces of H460 human non-small cell lung cancer malignant tumor tissue. When tumors reached the mean volume of approximately 90 mm$^3$, the animals was randomly assigned into different groups. Tumor volumes and body weight were measured once a week. At the end of the experiment mice were anesthetized and sacrificed. Tumors were carefully excised, weighed and were stored at −80° C. until further investigation. Organs and tumor samples were preserved in 10% formaldehyde.

TABLE XV

| Group | # of mice | Treatment |
| --- | --- | --- |
| Control | 9 | vehicle |
| Peptide 11602 | 7 | daily sc.injections of peptide 11602 (5 ug/day) |
| Peptide 11604 | 7 | daily sc.injections of peptide 11604 (5 ug/day) |
| Peptide 11606 | 7 | daily sc.injections of peptide 11606 (5 ug/day) |
| Peptide 11423 | 8 | daily sc.injections of peptide 11423 (5 ug/day) |

TABLE XVII

| | day 1 | day 7 | day 14 | day 21 | day 28 |
| --- | --- | --- | --- | --- | --- |
| Tumor Growth(%) | | | | | |
| Control | 100.00 | 529.86 | 1382.69 | 2469.01 | 4099.48 |
| peptide 11423 5 ug/day | 100.00 | 412.37 | 761.10 | 1130.90 | 2687.38 |
| peptide 11602 5 ug/day | 100.00 | 247.89 | 504.42 | 864.16 | 2575.35 |
| peptide-11604 5 ug/day | 100.00 | 341.87 | 609.38 | 1006.40 | 1595.34 |
| peptide 11606 5 ug/day | 100.00 | 221.26 | 494.68 | 933.19 | 1482.03 |
| Tumor inhibition (%) | | | | | |
| Control | | | | | |
| peptide11423 5 ug/day | | 22.17 | 44.95 | 54.20 | 34.45 |
| peptide 11602 5 ug/day | | 53.21 | 63.52 | 65.00 | 37.18 |
| peptide-11604 5 ug/day | | 35.48 | 55.93 | 59.24 | 61.08 |
| peptide 11606 5 ug/day | | 58.24 | 64.22 | 62.20 | 63.85 |

Example XVI

Protocol for HT Human Diffuse Mixed B Cell Lymphoma Cell Line Experiment

The aim of this study was to find out the tumor inhibitor effect of the latest GHRH antagonists (Peptide 11602, Peptide 11604, Peptide 11606, and Peptide 11610) at the dose of 5 ug/day on HT human diffuse mixed B cell lymphoma cell line. Female nude mice were xenografted subcutaneously with approximately 3 mm$^3$ pieces of HT malignant tumor tissue. When tumors reached the mean volume of approximately 120 mm$^3$, the animals were randomly assigned into different groups. Tumor volumes and body weight were measured once a week. At the end of the experiment mice were anesthetized and sacrificed. Tumors were carefully excised, weighed and were stored at −80° C. until further investigation. Organs and tumor samples were preserved in 10% formaldehyde.

TABLE XVII

| Group | # of mice | Treatment |
| --- | --- | --- |
| Control | 7 | vehicle |
| Peptide 11602 | 7 | daily sc.injections of peptide 11602 (5 ug/day) |
| Peptide 11604 | 7 | daily sc.injections of peptide 11604 (5 ug/day) |
| Peptide 11606 | 7 | daily sc.injections of peptide 11606 (5 ug/day) |
| Peptide 11610 | 7 | daily sc.injections of peptide 11610 (5 ug/day) |

TABLE XIX

HT human diffuse mixed B cell lymphoma cell line

| | Tumor volume (mm$^3$) | | | | |
| --- | --- | --- | --- | --- | --- |
| | day 1 | day 7 | day 14 | day 21 | day 28 |
| Control | 105.76 | 217.86 | 413.23 | 544.84 | 1188.23 |
| Peptide 11602 5 ug/day | 194.81 | 260.13 | 311.76 | 332.67 | 509.24 |
| Peptide 11604 5 ug/day | 125.04 | 165.21 | 231.44 | 563.86 | 818.2 |
| Peptide-11606 5 ug/day | 128.49 | 223.02 | 341.77 | 510.24 | 716.13 |
| Peptide 11610 5 ug/day | 90.42 | 145.53 | 194.57 | 250.24 | 428.99 |

TABLE XX

| | Tumor growth (%) | | | | |
| --- | --- | --- | --- | --- | --- |
| | day 1 | day 7 | day 14 | day 21 | day 28 |
| Control | 100 | 305.66 | 482.84 | 781.55 | 896.53 |
| P-11602 5 ug/day | 100 | 192.86 | 281.4 | 462.45 | 608.23 |
| P-11604 5 ug/day | 100 | 129.89 | 175.7 | 271.36 | 338.41 |
| P-11606 5 ug/day | 100 | 209.74 | 352.2 | 453.71 | 660.24 |
| P-11610 5 ug/day | 100 | 183.36 | 307.98 | 361.18 | 519.79 |

TABLE XXI

| | Tumor inhibition (%) | | | | |
| --- | --- | --- | --- | --- | --- |
| | day 1 | day 7 | day 14 | day 21 | day 28 |
| Control | | | | | |
| peptide 11602 5 ug/day | 0 | 36.94 | 41.71 | 40.82 | 32.15 |
| peptide 11604 5 ug/day | 0 | 57.53 | 63.61 | 65.27 | 62.25 |
| peptide-11606 5 ug/day | 0 | 31.38 | 27.05 | 41.94 | 26.35 |
| peptide 11610 5 ug/day | 0 | 40.01 | 36.21 | 53.78 | 42.02 |

Example XVII

Xenograft Ovarian Tumor Model of Ovarian Cancer Test

Human ovarian cancer SKOV3 cells growing exponentially were implanted info five female nude mice by subcutaneous (s.c.) injection of 10$^7$ cells in both flanks. Tumors That resulted after approximately 4 weeks in donor animals were then aseptically dissected and mechanically minced. Three mm$^3$ pieces of tumor tissue were transplanted subcutaneously into experimental animals with a trocar needle. When tumors reached an appropriate size (approximately 50 mm$^3$), mice were randomly divided into two groups. The first was the control group, the second group was treated with daily s.c. injections of 5 ug P-11313, the third group was treated with daily s.c. injections of 5 ug P-11604, the fourth group was treated with daily s.c. injections of 5 ug P-11610. Tumor volume (length×width×height×0.5236) was measured every week and mean tumor volumes of each group were compared by Student's t-test. The study lasted 49 days. One week after end of treatment, mice were killed under anesthesia, tumors were snap frozen and stored at −70° C.
Effects of P-11313, P-11604 and P-11610 on SKOV3 Ovarian Cancer Xenografts

|  | day 0 | day 7 | day 14 | day 21 | day 28 | day 35 | day 42 | day 49 |
|---|---|---|---|---|---|---|---|---|
| TU growth (%) | | | | | | | | |
| CONTROL | 100 | 214.38 | 280.25 | 543.5 | 842 | 892.83 | 1236 | 1272 |
| P-11313 5 ug/day | 100 | 147.84 | 140 | 196.6 | 249.65 | 201.5 | 274.05 | 328.63 |
| P-11604 5 ug/day | 100 | 144.55 | 174.5 | 179.5 | 167.5 | 182.88 | 397.95 | 309.96 |
| P-11610 5 ug/day | 100 | 137.44 | 150.1 | 239.14 | 204.07 | 242.05 | 273.83 | 383.93 |
| TU inhibition (%) | | | | | | | | |
| CONTROL | | | | | | | | |
| P-11313 5 ug/day | | 31.04 | 50.04 | 63.83 | 70.35 | 77.43 | 77.83 | 74.16 |
| P-11604 5 ug/day | | 32.57 | 37.73 | 66.97 | 80.12 | 79.52 | 67.80 | 75.63 |
| P-11610 5 ug/day | | 35.89 | 46.44 | 56.00 | 75.76 | 72.89 | 77.85 | 69.82 |

We claim:

1. A peptide selected from the group having the formulae:
[$A^0$-Tyr$^1$, D-Arg$^2$, $A^4$, $A^6$, $A^8$, Har$^9$, Tyr(Me)$^{10}$, $A^{11}$, $A^{12}$, Abu$^{15}$, $A^{17}$, $A^{20}$, $A^{21}$, Nle$^{27}$, D-Arg$^{28}$, $A^{29}$-$A^{30}$-$A^{31}$] hGH-RH(1-29)NH$_2$
wherein
$A^0$ is PhAc, N-Me-Aib, Dca, Ac-Ada, Fer, Ac-Amc, Me-NH-Sub, PhAc-Ada, Ac-Ada-D-Phe, Ac-Ada-Phe, Dca-Ada, Dca-Amc, Nac-Ada, Ada-Ada, or CH$_3$—(CH$_2$)$_{10}$—CO-Ada,
$A^4$ is Ala or Me-Ala,
$A^6$ is Cpa or Phe(F)$_5$,
$A^8$ is Ala, Pal, or Me-Ala,
$A^{11}$ is His or Arg,
$A^{12}$ is Lys, Lys(0-11), Lys(Me)$_2$ or Orn,
$A^{17}$ is Leu or Glu,
$A^{20}$ is Har or His,
$A^{21}$ is -Lys, Lys(Me)$_2$ or Orn,
$A^{29}$ is Har, Arg or Agm,
$A^{30}$ is absent, β-Ala, Amc, Apa, Ada, AE$_2$A, AE$_4$P, ε-Lys (α-NH$_2$) or Agm,
$A^{31}$ is absent, Lys(Oct) or Ahx,
provided that where $A^0$ is PhAc, $A^{12}$ and $A^{21}$ are both other than Orn and $A^{30}$ is not absent and is not Agm, and pharmaceutically acceptable salts thereof.

2. The peptide of claim 1 selected from the group having the formulae:
[$A^0$-Tyr$^1$, D-Arg$^2$, Ala$^4$, $A^6$, $A^8$, Har$^9$, Tyr(Me)$^{10}$, His$^{11}$, $A^{12}$, Abu$^{15}$, $A^{17}$, His$^{20}$, $A^{21}$, Nle$^{27}$, D-Arg$^{28}$, Har$^{29}$-$A^{30}$] hGH-RH(1-29)NH$_2$
wherein $A^0$ is PhAc, Dca, Ac-Ada, Fer, Ac-Amc, PhAc-Ada, Ac-Ada-D-Phe, Dca-Ada, Dca-Amc, or CH$_3$—(CH$_2$)$_{10}$—CO-Ada, $A^6$ is Cpa or Phe(F)$_5$, $A^8$ is Ala or Me-Ala, $A^{12}$ is Lys, or Orn, $A^{17}$ is Leu or Glu, $A^{21}$ is -Lys, or Orn, $A^{30}$ is absent, Amc, Apa, Ada, AE$_2$A, or Agm, provided that where $A^0$ is PhAc, $A^{12}$ and $A^{21}$ are both other than Orn and $A^{30}$ is not absent and is not Agm, and pharmaceutically acceptable salts thereof.

3. The peptide of claim 2 selected from the group having the formulae: wherein $A^0$ is Dca, Ac-Ada, Ac-Amc, PhAc-Ada, Dca-Ada, or CH$_3$—(CH$_2$)$_{10}$—CO-Ada and $A^{30}$ is Agm, Ada, or absent.

4. The peptide of claim 1 selected from the group having the formulae:

P-11107 [(N—Me-Aib)$^0$-Tyr$^1$, D-Arg$^2$, Cpa$^6$, Ala$^8$, Har$^9$, Tyr(Me)$^{10}$, His$^{11}$, Abu$^{15}$, His$^{11}$, Nle$^{27}$, D-Arg$^{28}$, Har$^{29}$]hGH-RH(1-29)NH$_2$,

P-11109 [Dca$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11111 [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11113 [Fer$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11115 [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11117 [(PhAc-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11119 [(Ac-Ada-D-Phe)$^0$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11121 [(Ac-Ada-Phe)$^0$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11123 [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^2$8, Har$^{29}$]hGH-RH(1-29)NH$_2$,

P-11125 [CH$_3$—(CH$_2$)$_{10}$—CO-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11207 [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$,

P-11209 [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Apa$^{30}$]hGH-RH(1-29)NH$_2$,

P-11211 [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$,

P-11215 [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$]hGH-RH(1-29)NH$_2$,

P-11311 [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Agm$^{29}$]hGH-RH(1-29),

P-11313 [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Agm$^{30}$]hGH-RH(1-29),

P-11315 [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$,

P-11317 [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$,

P-11321 [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$]hGH-RH(1-29)NH$_2$,

P-11407 [(Ac-Amc)$^0$-Tyr$^1$, D-Arg$^2$, (Me-Ala)$^4$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11408 [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11409 [(Ac-Amc)$^0$-Tyr$^1$, D-Arg$^2$, (Me-Ala)$^4$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11411 [PhAc$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$,

P-11415 [(Ac-Amc$^0$)-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^2$7, D-Arg$^{28}$, Har$^{29}$-Agm$^{30}$]hGH-RH(1-29),

P-11417 [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$,

P-11419 [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$,

-continued

P-11421 [(N—Me-Aib$^0$)-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$,

P-11427 [(N—Me-Aib)$^0$-Tyr$^1$, D-Arg$^2$, Cpa$^6$, Ala$^8$, Har$^9$, Tyr(Me)$^{10}$, His$^{11}$, Lys(0-11)$^{12}$, Abu$^{15}$, His$^{20}$, Orn$^{21}$, Nle$^{27}$, D-Arg$^{28}$, Har$^{29}$ wherein (0-11) is N-Me-Aib-Tyr-D-Arg-Asp-Ala-Ile-Cpa-Thr-Ala-Har-Tyr(Me)-His- and the C-terminal carbonyl group of the (0-11) peptide sequence forms an amide bond with the epsilon amino group of Lys$^{12}$, P-11429 [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-(β-Ala$^{30}$-Lys(Oct)$^{31}$]hGH-RH(1-29)NH$_2$, P-11431 [(N—Me-Aib)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$, P-11435 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11437 [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11439 [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, P-11441 [(Ac-Ada)$^0$-Tyr$^1$, D-Arg$^2$, Cpa$^6$, Ala$^8$, Har$^9$, Tyr(Me)$^{10}$, His$^{11}$, (Lys(Me)$_2$)$^{12}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, P-11443 [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, P-11445 [(Dca-Ada)$^0$-Tyr$^1$, D-Arg$^2$, Cpa$^6$, Ala$^8$, Har$^9$, Tyr(Me)$^{10}$, His$^{11}$, (Lys(Me)$_2$)$^{12}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, P-11449 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Har$^{20}$, Orn$^{21}$, Nle$^{27}$, D-Arg$^{28}$, Har$^{29}$]hGH-RH(1-29)NH$_2$, P-11451 [(Nac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, P-11453 [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, P-11455 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, P-11457 [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11459 [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11461 [(Ac-Ada-Phe)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11463 [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Amc$^{30}$]hGH-RH(1-29)NH$_2$, P-11465 [PhAc$^0$-Tyr$^1$, D-Arg$^2$, Cpa$^6$, Ala$^8$, Har$^9$, Tyr(Me)$^{10}$, His$^{11}$, Abu$^{12}$, His$^{20}$, Orn$^{21}$, Nle$^{27}$, D-Arg$^{28}$, Har$^{29}$-Ada$^{30}$]hGH-RH(1-29)NH$_2$, P-11467 [(Ada-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11469 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11471 [(Ac-Ada)$^0$-Tyr$^1$, D-Arg$^2$, Cpa$^6$, Ala$^8$, Har$^9$, Tyr(Me)$^{10}$, His$^{11}$, Lys(0-11)$^{12}$, Abu$^{15}$, His$^{20}$, Orn$^{21}$, Nle$^{27}$, D-Arg$^{28}$, Har$^{29}$ wherein (0-11) is PhAc-Tyr-D-Arg-Asp-Ala-Ile-Cpa-Thr-Ala-Har-Tyr(Me)-His- and the C-terminal carbonyl group of the (0-11) peptide sequence forms an amide bond with the epsilon amino group of Lys$^{12}$, P-11473 [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11475 [(Ac-Ada-D-Phe)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, -continued P-11477 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, His$^{20}$, Nle$^{27}$, D-Arg$^{28}$, Har$^{29}$]hGH-RH(1-29)NH$_2$, P-11479 [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11481 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$ ε-Lys(α-NH$_2$)$^{30}$-Ahx$^{31}$]hGH-RH(1-29)NH$_2$, P-11483 [(Ac-Ada)0-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_4$P$^{30}$]hGH-RH(1-29)NH$_2$, P-11485 [(CH$_3$-(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11487 [(CH$_3$-(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11491 [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11497 [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$hGH-RH(1-29)NH$_2$, P-11499 [PhAc$^0$-Tyr$^1$, D-Arg$^2$, (Phe(F)5)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11501 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$, P-11503 [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-β-Ala$^{30}$-Lys(Oct)$^{31}$]hGH-RH(1-29)NH$_2$, P-11513 [Dca$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Har$^{20}$, Orn$^{21}$, Nle$^{27}$, D-Arg$^{28}$, Har$^{29}$]hGH-RH(1-29)NH$_2$, P-11515 [(Dca-Ada)$^0$-Tyr$^1$, D-Arg$^2$, Cpa$^6$, Ala$^8$, Har$^9$, Tyr(Me)$^{10}$, His$^{11}$, Lys(0-11)$^{12}$, Abu$^{15}$, His$^{20}$, Orn$^{21}$, Nle$^{27}$, D-Arg$^{28}$, Har$^{29}$] wherein (0-11) is PhAc-Tyr-D-Arg-Asp-Ala-Ile-Cpa-Thr-Ala-Har-Tyr(Me)-His- and the C-terminal carbonyl group of the (0-11) peptide sequence forms an amide bond with the epsilon amino group of Lys$^{12}$, P-11601 [(CH$_3$-(CH$_2$)$^{10}$-CO-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11602 [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, P-11603 [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, P-11611 [(Ac-Amc)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11612 [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$, P-11620 [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Arg$^{29}$-Ada$^{30}$]hGH-RH(1-29)NH$_2$, P-11621 [(Me-NH-Sub)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$, P-11629 [(Ac-Ada)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$, P-11701 [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, Orn$^{21}$, Nle$^{27}$, D-Arg$^{28}$, Har$^{29}$-AE$_4$P$^{30}$]hGH-RH(1-29)NH$_2$, P-11702 [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, His$^{20}$, Orn$^{21}$, Nle$^{27}$, D-Arg$^{28}$, Har$^{29}$-AE$_4$P$^{30}$]hGH-RH(1-29)NH$_2$, P-11703 [(Dca-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Glu$^{17}$, Har$^{20}$, Orn$^{21}$, Nle$^{27}$, D-Arg$^{28}$, Har$^{29}$-AE4P$^{30}$, and P-11704 [(CH$_3$-(CH$_2$)$_{10}$-CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_4$P$^{30}$]hGH-RH(1-29)NH$_2$.

5. The peptide of claim 2 selected from the group having the formulae:

P-11109 [Dca$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11111 [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11113 [(Fer$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11115 [(Ac-Amc)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11117 [(PhAc-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11119 [(Ac-Ada-D-Phe)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11123 [(Dca-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11125 [(CH$_3$—(CH$_2$)$_{10}$—CO-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11209 [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Apa$^{30}$]hGH-RH(1-29)NH$_2$,

P-11313 [(Ac-Amc)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Nle$^{27}$, D-Arg$^{28}$, Har$^{29}$-Agm$^{30}$]hGH-RH(1-29),

P-11317 [(Ac-Ada)$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Nle$^{27}$, D-Arg$^{28}$, Har$^{29}$-Ada$^{30}$]hGH-RH(1-29)NH$_2$,

P-11408 [(Ac-Amc)$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$,

P-11435 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$,

P-11457 [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$,

P-11459 [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$,

P-11469 [(Ac-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$,

P-11473 [(PhAc-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$,

P-11479 [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$,

P-11485 [(CH$_3$—(CH$_2$)$_{10}$CO-Ada)$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29),NH$_2$,

P-11491 [(Dca-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$,

P-11497 [(Ac-Amc)$^0$-Tyr$^1$, D-Arg$^2$, Cpa$^6$, Ala$^8$, Har$^9$, Tyr(Me)$^{10}$, His$^1$1, Orn$^1$2, Abu$^{15}$, His$^{20}$, Orn21, Nle$^{27}$, D-Arg$^{28}$, Har$^{29}$-Ada$^{30}$]hGH-RH(1-29)NH$_2$,

P-11499 [PhAc$^0$-Tyr$^1$, D-Arg$^2$, (Phe(F)5)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$,

P-11601 [(CH$_3$—(CH$_2$)$_{10}$—CO-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$,

P-11602 [(PhAc-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$, and P-11612 [(Ac-Ada)$^0$-Tyr$^1$, D-Arg$^2$, (Phe(F)$_5$)$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-Ada$^{30}$]hGH-RH(1-29)NH$_2$.

6. The peptide of claim 1 selected from the group having the formulae:

```
P-11109  [Dca⁰-Tyr¹, D-Arg², Cpa⁶, Ala⁸, Har⁹, Tyr(Me)¹⁰, His¹¹, Abu¹⁵, His²⁰, Nle²⁷,
         D-Arg²⁸, Har²⁹]hGH-RH(1-29)NH₂,

P-11113  [Fer⁰-Tyr¹, D-Arg², Cpa⁶, Ala⁸, Har⁹, Tyr(Me)¹⁰, His¹¹, Abu¹⁵, His²⁰, Nle²⁷,
         D-Arg²⁸, Har²⁹]hGH-RH(1-29)NH₂,

P-11117  [(PhAc-Ada)⁰-Tyr¹, D-Arg², Cpa⁶, Ala⁸, Har⁹, Tyr(Me)¹⁰, His¹¹, Abu¹⁵,
         His²⁰, Nle²⁷, D-Arg²⁸, Har²⁹]hGH-RH(1-29)NH₂,

P-11119  [(Ac-Ada-D-Phe)⁰-Tyr¹, D-Arg², Cpa⁶, Ala⁸, Har⁹, Tyr(Me)¹⁰, His¹¹, Abu¹⁵,
         His²⁰, Nle²⁷, D-Arg²⁸, Har²⁹]hGH-RH(1-29)NH₂,

P-11123  [(Dca-Ada)⁰-Tyr¹, D-Arg², Cpa⁶, Ala⁸, Har⁹, Tyr(Me)¹⁰, His¹¹, Abu¹⁵, His²⁰,
         Nle²⁷, D-Arg²⁸, Har²⁹]hGH-RH(1-29)NH₂,

P-11125  [CH₃—(CH₂)₁₀—CO-Ada)⁰-Tyr¹, D-Arg², Cpa⁶, Ala⁸, Har⁹, Tyr(Me)¹⁰, His¹¹,
         Abu¹⁵, His²⁰, Nle²⁷, D-Arg²⁸, Har²⁹]hGH-RH(1-29)NH₂,

P-11213  [Oct⁰-Tyr¹, D-Arg², Cpa⁶, Ala⁸, His⁹, Tyr(Et)¹⁰, His¹¹, Orn¹², Abu¹⁵, His²⁰,
         Orn²¹, Nle²⁷, D-Arg²⁸, Har²⁹-Ada³⁰]hGH-RH(1-29)NH₂,

P-11313  [(Ac-Amc)⁰-Tyr¹, D-Arg², Cpa⁶, Ala⁸, Har⁹, Tyr(Me)¹⁰, His¹¹, Orn¹², Abu¹⁵,
         His²⁰, Nle²⁷, D-Arg²⁸, Har²⁹-Agm³⁰]hGH-RH(1-29)NH₂,

P-11317  [(Ac-Ada)⁰-Tyr¹, D-Arg², Cpa⁶, Ala⁸, Har⁹, Tyr(Me)¹⁰, His¹¹, Abu¹⁵, His²⁰,
         Nle²⁷, D-Arg²⁸, Har²⁹-Ada]hGH-RH(1-29)NH₂,

P-11408  [(Ac-Amc)⁰-Tyr¹, D-Arg², Cpa⁶, (Me-Ala)⁸, Har⁹, Tyr(Me)¹⁰, His¹¹, Abu¹⁵,
         His²⁰, Nle²⁷, D-Arg²⁸, Har²⁹]hGH-RH(1-29)NH₂,

P-11435  [(Ac-Ada)⁰-Tyr¹, D-Arg², Cpa⁶, Ala⁸, Har⁹, Tyr(Me)¹⁰, His¹¹, Orn¹², Abu¹⁵,
         His²⁰, Orn²¹, Nle²⁷, D-Arg²⁸, Har²⁹]hGH-RH(1-29)NH₂,

P-11457  [PhAc⁰-Tyr¹, D-Arg², Cpa⁶, Ala⁸, Har⁹, Tyr(Me)¹⁰, His¹¹, Orn¹², Abu¹⁵,
         His²⁰, Orn²¹, Nle²⁷, D-Arg²⁸, Har²⁹-Ada³⁰]hGH-RH(1-29)NH₂,

P-11459  [(PhAc-Ada)⁰-Tyr¹, D-Arg², Cpa⁶, Ala⁸, Har⁹, Tyr(Me)¹⁰, His¹¹, Orn¹²,
         Abu¹⁵, His²⁰, Orn²¹, Nle²⁷, D-Arg²⁸, Har²⁹]hGH-RH(1-29)NH₂,

P-11469  [(Ac-Ada)⁰-Tyr¹, D-Arg², Cpa⁶, Ala⁸, Har⁹, Tyr(Me)¹⁰, His¹¹, Orn¹², Abu¹⁵,
         His²⁰, Orn²¹, Nle²⁷, D-Arg²⁸, Har²⁹-Ada³⁰]hGH-RH(1-29)NH₂,

P-11473  [(PhAc-Ada)⁰-Tyr¹, D-Arg², Cpa⁶, Ala⁸, Har⁹, Tyr(Me)¹⁰, His¹¹, Orn¹²,
         Abu¹⁵, His²⁰, Orn²¹, Nle²⁷, D-Arg²⁸, Har²⁹-Ada³⁰]hGH-RH(1-29)NH₂,

P-11485  [(CH₃—(CH₂)₁₀—Co-Ada)⁰-Tyr¹, D-Arg², Cpa⁶, Ala⁸, Har⁹, Tyr(Me)¹⁰, His¹¹,
         Orn¹², Abu¹⁵, His²⁰, Orn²¹, Nle²⁷, D-Arg²⁸, Har²⁹-Ada³⁰]hGH-RH(1-29)NH₂,

P-11491  [(Dca-Ada)⁰-Tyr¹, D-Arg², (Phe(F)5)⁶, Ala⁸, Har⁹, Tyr(Me)¹⁰, His¹¹, Orn¹²,
         Abu¹⁵, His²⁰, Orn²¹, Nle²⁷, D-Arg²⁸, Har²⁹]hGH-RH(1-29)NH₂,

P-11601  [(CH₃—(CH₂)₁₀—CO-Ada)⁰-Tyr¹, D-Arg², (Phe(F)5)⁶, Ala⁸, Har⁹, Tyr(Me)¹⁰,
         His¹¹, Orn¹², Abu¹⁵, His²⁰, Orn²¹, Nle²⁷, D-Arg²⁸, Har²⁹]hGH-RH(1-29)NH₂,
         and P-11602  [(PhAc-Ada)⁰-Tyr¹, D-Arg², (Phe(F)5)⁶, Ala⁸, Har⁹, Tyr(Me)¹⁰, His¹¹, Orn¹²,
         Abu¹⁵, His²⁰, Orn²¹, Nle²⁷, D-Arg²⁸, Har²⁹]hGH-RH(1-29)NH₂.
```

7. A peptide selected from the group having the formulae:
[PhAc⁰-Tyr¹, D-Arg², Cpa⁶, Ala⁸, Har⁹, (Phe(F)₅)¹⁰, His¹¹, Orn¹², Abu¹⁵, His²⁰, Orn²¹, Nle²⁷, D-Arg²⁸, Har²⁹-Ada³⁰] hGH-RH(1-29)NH₂ (P-11610) and pharmaceutically acceptable salts thereof.

8. A GHRH peptide of the formula:
[(PhAc-Ada)⁰-Tyr¹, D-Arg², (Phe(F)₅)⁶, Ala⁸, Har⁹, Tyr(Me)¹⁰, His¹¹, Orn¹², Abu¹⁵, His²⁰, Orn²¹, Nle²⁷, D-Arg²⁸, Har²⁹]hGH-RH(1-29)NH₂ (P-11602) and pharmaceutically acceptable salts thereof.

9. A peptide selected from the group having the formula:

```
P-1109  [PhAc⁰-Tyr¹, D-Arg², Cpa⁶, Ala⁸, Har⁹, Tyr(Me)¹⁰, His¹¹, Abu¹⁵, Glu¹⁷,
        His²⁰, Nle²⁷, D-Arg²⁸, Har²⁹]hGH-RH(1-29)NH₂,

P-1111  [PhAc⁰-Tyr¹, D-Arg², (Me-Ala)⁴, Cpa⁶, Ala⁸, Har⁹, Tyr(Me)¹⁰, His¹¹, Abu¹⁵,
        His²⁰, Nle²⁷, D-Arg²⁸, Har²⁹]hGH-RH(1-29)NH₂,
```

|         |                                                                                                                                                                                                                                                                                                                           |
|---------|---------------------------------------------------------------------------------------------------------------------------------------------------------------------------------------------------------------------------------------------------------------------------------------------------------------------------|
| P-1113  | [PhAc$^0$-Tyr$^1$, D-Arg$^2$, Cpa$^6$, (Me-Ala)$^8$, Har$^9$, Tyr(Me)$^{10}$, His$^{11}$, Abu$^{15}$, His$^{20}$, Nle$^{27}$, D-Arg$^{28}$, Har$^{29}$]hGH-RH(1-29)NH$_2$, |
| P-1115  | [PhAc$^0$-Tyr$^1$, D-Arg$^2$, Cpa$^6$, Ala$^8$, Har$^9$, Tyr(Me)$^{10}$, His$^{11}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, |
| P-1117  | [PhAc$^0$-Tyr$^1$, D-Arg$^2$, Cpa$^6$, Ala$^8$, Har$^9$, Tyr(Me)$^{10}$, His$^{11}$, (Lys(Me)$_2$)$^{12}$, Abu$^{15}$, His$^{20}$, (Lys(Me)$_2$)$^{21}$, Nle$^{27}$, D-Arg$^{28}$, Har$^{29}$]hGH-RH(1-29)NH$_2$, |
| P-11213 | [Oct$^0$-Tyr$^1$, D-Arg$^2$, Cpa$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$-Ada]hGH-RH(1-29)NH$_2$, |
| P-11319 | [(Ac-Ada)$^0$-Tyr$^1$, D-Arg$^2$, Cpa$^6$, Ala$^8$, His$^9$, Tyr(Et)$^{10}$, His$^{11}$, Orn$^{12}$, Abu$^{15}$, His$^{20}$, Orn$^{21}$, Nle$^{27}$, D-Arg$^{28}$, Har$^{29}$-Ada]hGH-RH(1-29)NH$_2$, |
| P-11423 | [PhAc$^0$-Tyr$^1$, D-Arg$^2$, Cpa$^6$, Dip$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$-AE$_2$A$^{30}$]hGH-RH(1-29)NH$_2$, |
| P-11425 | [PhAc$^0$-Tyr$^1$, D-Arg$^2$, Cpa$^6$, Ala$^8$, Har$^9$, Tyr(Me)$^{10}$, His$^{11}$, Lys(0-11)$^{12}$, Abu$^{15}$, His$^{20}$, Orn$^{21}$, Nle$^{27}$, D-Arg$^{28}$, Har$^{29}$]hGH-RH(1-29)NH$_2$ wherein (0-11) is PhAc-Tyr-D-Arg-Asp-Ala-Ile-Cpa-Thr-Ala-Har-Tyr(Me)-His and the C-terminal carbonyl group of the (0-11) peptide sequence forms an amide bond with the epsilon amino group of Lys$^{12}$, |
| P-11433 | [Nac$^0$-Tyr$^1$, D-Arg$^2$, Cpa$^6$, Ala$^8$, Har$^9$, Tyr(Me)$^{10}$, His$^{11}$, Abu$^{15}$, His$^{20}$, Orn$^{21}$, Nle$^{27}$, D-Arg$^{28}$, Har$^{29}$]hGH-RH(1-29)NH$_2$, |
| P-11447 | [PhAc$^0$-Tyr$^1$, D-Arg$^2$, Cpa$^6$, Ala$^8$, Har$^9$, Tyr(Me)$^{10}$, His$^{11}$, Orn$^{12}$, Abu$^{15}$, Har$^{20}$, Orn$^{21}$, Nle$^{27}$, D-Arg$^{28}$, Har$^{29}$]hGH-RH(1-29)NH$_2$, |
| P-11521 | [(Dca-Amc)$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, His$^{20}$, Orn$^{21}$, Nle$^{27}$, D-Arg$^{28}$, Har$^{29}$-Ada$^{30}$]hGH-RH(1-29)NH$_2$, |
| P-11523 | [PhAc$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, Glu$^{17}$, His$^{20}$, Orn$^{21}$, Nle$^{27}$, D-Arg$^{28}$, Har$^{29}$-Ada$^{30}$]hGH-RH(1-29)NH$_2$, |
| P-11525 | [PhAc$^0$-Tyr$^1$, D-Arg$^2$, Cpa$^6$, Ala$^8$, Har$^9$, Tyr(Me)$^{10}$, His$^{11}$, Orn$^{12}$, Orn$^{15}$, His$^{20}$, Orn$^{21}$, Nle$^{27}$, D-Arg$^{28}$, Har$^{29}$-Ada$^{30}$]hGH-RH(1-29)NH$_2$, and |
| P-11413 | [PhAc$^0$-Tyr$^1$, D-Arg$^2$, Cpa$^6$, 3-Pal$^8$, Har$^9$, Tyr(Me)$^{10}$, His$^{11}$, Abu$^{15}$, His$^{20}$, Nle$^{27}$, D-Arg$^{28}$, Har$^{29}$-Amc$^{30}$]hGH-RH(1-29)NH$_2$. |

* * * * *